US010238718B2

(12) United States Patent
Liebing et al.

(10) Patent No.: US 10,238,718 B2
(45) Date of Patent: Mar. 26, 2019

(54) FACTOR VIII FORMULATION

(71) Applicant: CSL LIMITED, Parkville, Victoria (AU)

(72) Inventors: Uwe Liebing, Coelbe (DE); Hubert Metzner, Marburg (DE); Christina Bodenbender, Lohra (DE)

(73) Assignee: CSL LIMITED, Parkville (AU)

( * ) Notice: Subject to any disclaimer, the term of this patent is extended or adjusted under 35 U.S.C. 154(b) by 0 days.

(21) Appl. No.: 15/501,059

(22) PCT Filed: Jul. 24, 2015

(86) PCT No.: PCT/EP2015/066999
§ 371 (c)(1),
(2) Date: Feb. 1, 2017

(87) PCT Pub. No.: WO2016/020210
PCT Pub. Date: Feb. 11, 2016

(65) Prior Publication Data
US 2017/0252412 A1 Sep. 7, 2017

(30) Foreign Application Priority Data
Aug. 4, 2014 (EP) .................................... 14179732

(51) Int. Cl.
| *A61K 38/00* | (2006.01) |
| *A61K 38/37* | (2006.01) |
| *A61K 9/19* | (2006.01) |
| *A61K 9/00* | (2006.01) |
| *A61K 47/02* | (2006.01) |
| *A61K 47/18* | (2017.01) |
| *A61K 47/26* | (2006.01) |
| *A61K 9/08* | (2006.01) |
| *A61K 47/20* | (2006.01) |
| *A61K 47/22* | (2006.01) |

(52) U.S. Cl.
CPC ............ *A61K 38/37* (2013.01); *A61K 9/0019* (2013.01); *A61K 9/0095* (2013.01); *A61K 9/08* (2013.01); *A61K 9/19* (2013.01); *A61K 47/02* (2013.01); *A61K 47/183* (2013.01); *A61K 47/20* (2013.01); *A61K 47/22* (2013.01); *A61K 47/26* (2013.01)

(58) Field of Classification Search
None
See application file for complete search history.

(56) References Cited

U.S. PATENT DOCUMENTS

| 4,877,608 | A | 10/1989 | Lee et al. |
| 5,565,427 | A | 10/1996 | Freudenberg |
| 5,605,884 | A | 2/1997 | Lee et al. |
| 5,733,873 | A | 3/1998 | Österberg et al. |
| 5,763,401 | A | 6/1998 | Nayar |
| 5,874,408 | A | 2/1999 | Nayar |
| 2005/0256038 | A1 | 11/2005 | White et al. |
| 2007/0021338 | A1* | 1/2007 | Hansen ............... A61K 9/0019 514/14.1 |
| 2008/0064856 | A1 | 3/2008 | Warne et al. |
| 2010/0113364 | A1 | 5/2010 | Turecek et al. |
| 2010/0113365 | A1 | 5/2010 | Turecek et al. |
| 2010/0168391 | A1 | 7/2010 | Siekmann et al. |
| 2010/0173830 | A1 | 7/2010 | Turecek et al. |
| 2010/0173831 | A1 | 7/2010 | Turecek et al. |

FOREIGN PATENT DOCUMENTS

| EP | 0 410 207 A2 | 1/1991 | |
| EP | 0 511 234 B1 | 4/1995 | |
| EP | 0 871 476 B1 | 7/2003 | |
| EP | 0 819 010 B1 | 10/2003 | |
| EP | 0 638 091 B1 | 12/2005 | |
| EP | 1 712 223 A1 | 10/2006 | |
| EP | 1712223 A1 * | 10/2006 | ............... A61K 9/19 |
| EP | 2 361 613 A1 | 8/2011 | |
| WO | WO 91/10439 | 7/1991 | |
| WO | WO 93/22336 | 11/1993 | |
| WO | WO 96/22107 | 7/1996 | |
| WO | WO 96/30041 | 10/1996 | |
| WO | WO 00/48635 | 8/2000 | |
| WO | WO 03/031464 A2 | 4/2003 | |
| WO | WO 2004/067566 A1 | 8/2004 | |
| WO | WO 2005/058283 A2 | 6/2005 | |
| WO | WO 2007/126808 A1 | 11/2007 | |
| WO | WO 2008/077616 A1 | 7/2008 | |
| WO | WO 2008/082669 A2 | 7/2008 | |
| WO | WO 2008/135501 A1 | 11/2008 | |
| WO | WO 2009/007451 A1 | 1/2009 | |
| WO | WO 2009/062100 A1 | 5/2009 | |
| WO | WO 2009/108806 A1 | 9/2009 | |
| WO | WO 2010/014708 A2 | 2/2010 | |
| WO | WO 2010/045568 A1 | 4/2010 | |
| WO | WO 2010/054238 A1 | 5/2010 | |
| WO | WO 2010/102886 A1 | 9/2010 | |

(Continued)

OTHER PUBLICATIONS

International Search Report and Written Opinion, dated Sep. 4, 2015, in International Patent Application No. PCT/EP2015/066999, 11 pages.
European Search Report and Search Opinion, dated Dec. 10, 2014, in European Patent Application No. 14179732.4, 8 pages.
Lee et al., "An Effect of Predilution on Potency Assays of Factor VIII Concentrates," Thrombosis Research, 30; 511-519 (1983).
"Scientific Discussion," EMEA 2004, pp. 1-13.

(Continued)

*Primary Examiner* — Jeanette M Lieb
(74) *Attorney, Agent, or Firm* — Finnegan, Henderson, Farabow, Garrett & Dunner, L.L.P.

(57) ABSTRACT

The invention relates to factor VIII compositions and their use.

24 Claims, 1 Drawing Sheet
Specification includes a Sequence Listing.

(56) References Cited

FOREIGN PATENT DOCUMENTS

| | | |
|---|---|---|
| WO | WO 2010/115866 A1 | 10/2010 |
| WO | WO 2011/027152 A1 | 3/2011 |
| WO | WO 2011/101242 A1 | 8/2011 |
| WO | WO 2011/101267 A1 | 8/2011 |
| WO | WO 2011/101277 A1 | 8/2011 |
| WO | WO 2011/101284 A1 | 8/2011 |
| WO | WO 2011/131510 A2 | 10/2011 |
| WO | WO 2012/007324 A2 | 1/2012 |
| WO | WO 2012/037530 A1 | 3/2012 |
| WO | WO 2013/057219 A1 | 4/2013 |
| WO | WO-2013057219 A1 * | 4/2013 ............ A61K 38/37 |
| WO | WO 2013/083858 A1 | 6/2013 |
| WO | WO 2014/026954 A1 | 2/2014 |

OTHER PUBLICATIONS

"2.6.8. Pyrogens," European Pharmacopoeia 8.8, p. 5923.
"2.2.1. Clarity and degree of opalescence of liquids," European Pharmacopoeia 8.0, pp. 21-22.

* cited by examiner

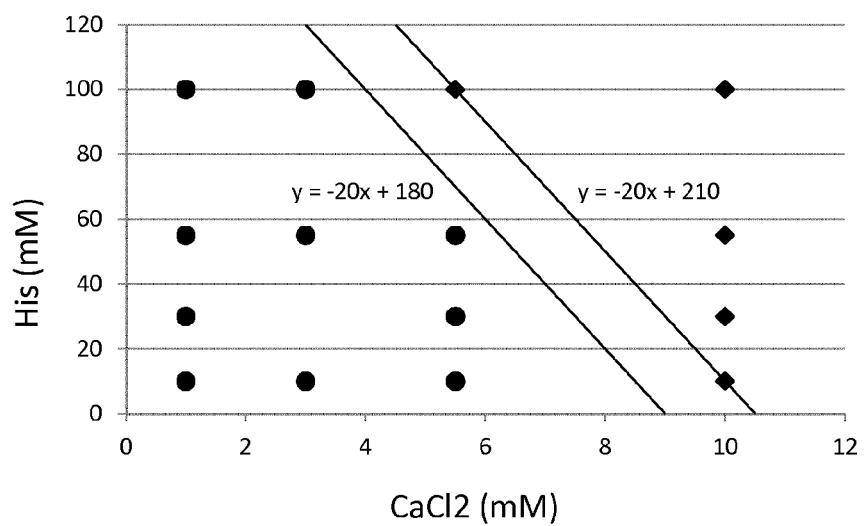

FACTOR VIII FORMULATION

This application is the United States national stage entry under 35 U.S.C. § 371 of International Application No. PCT/EP2015/066999, filed on Jul. 24, 2015 and published as WO 2016/020210 A1, which claims priority to European Patent Application No. 14179732.4, filed on Aug. 4, 2014. The contents of these applications are each incorporated herein by reference in their entirety.

BACKGROUND OF THE INVENTION

Factor VIII (FVIII) is a protein found in blood plasma, which acts as a cofactor in the cascade of reactions leading to blood coagulation. A deficiency in the amount of FVIII activity in the blood results in the clotting disorder known as hemophilia A, an inherited condition primarily affecting males. Hemophilia A is currently treated with therapeutic preparations of FVIII derived from human plasma or manufactured using recombinant DNA technology. Such preparations are administered either in response to a bleeding episode (on-demand therapy) or at frequent, regular intervals to prevent uncontrolled bleeding (prophylaxis).

FVIII is known to be relatively unstable in therapeutic preparations. In blood plasma, FVIII is usually complexed with another plasma protein, von Willebrand factor (vWF), which is present in plasma in a large molar excess of the VWF subunit to FVIII and is believed to protect FVIII from premature degradation. Another circulating plasma protein, albumin, may also play a role in stabilizing FVIII in vivo. Currently marketed FVIII preparations therefore often rely on the use of albumin and/or vWF to stabilize FVIII during the manufacturing process and during storage.

The albumin and vWF used in currently marketed FVIII preparations are derived from human blood plasma, however, and the use of such material has certain drawbacks. A large molar excess of albumin compared to FVIII is typically added in order to increase the stability of the FVIII in such preparations, and this makes it more difficult to characterize the FVIII protein itself in these preparations. The addition of human-derived albumin to FVIII is also perceived as being a disadvantage with respect to recombinantly-produced FVIII preparations. This is because, in the absence of such added albumin, the theoretical risk of transmitting a virus would be reduced in recombinantly-derived FVIII preparations.

Several attempts to formulate FVIII without albumin or vWF (or with relatively low levels of these excipients) have been described. For example, U.S. Pat. No. 5,565,427 (EP 508 194) describes FVIII preparations which contain particular combinations of detergent and amino acids, specifically arginine and glycine, in addition to excipients such as sodium chloride and sucrose.

U.S. Pat. No. 5,763,401 (EP 818 204) also describes a therapeutic FVIII formulation without albumin, comprising 15-60 mM sucrose, up to 50 mM NaCl, up to 5 mM calcium chloride, 65-400 mM glycine, and up to 50 mM histidine.

U.S. Pat. No. 5,733,873 (EP 627 924) to Osterberg (assigned to Pharmacia & Upjohn) discloses formulations which include between 0.01-1 mg/ml of a surfactant.

Other attempts to use low or high concentrations of sodium chloride have also been described. U.S. Pat. No. 4,877,608 (EP 315 968) discloses formulations with relatively low concentrations of sodium chloride, namely 0.5 mM to 15 mM NaCl.

On the other hand, U.S. Pat. No. 5,605,884 (EP 0 314 095) teaches the use of formulations with relatively high concentrations of sodium chloride.

Further FVIII formulations are disclosed in WO 2010/054238, EP 1 712 223, WO 2000/48635, WO 96/30041, WO 96/22107, WO 2011/027152, EP 2 361 613, EP 0 410 207, EP 0 511 234, U.S. Pat. No. 5,565,427, EP 0 638 091, EP 0 871 476, EP 0 819 010, U.S. Pat. No. 5,874,408, US 2005/0256038, US 2008/0064856, WO 2005/058283, WO 2012/037530 and WO 2014/026954. EP 1 712 223 A1 discloses FVIII compositions comprising histidine and $CaCl_2$, but the combined concentrations of histidine and $Ca^{2+}$ in the compositions of EP 1 712 223 A1 are too low to confer the desired FVIII stability in aqueous solution.

Other therapeutic FVIII formulations of the prior art generally include albumin and/or vWF for the purpose of stabilizing FVIII and are therefore not relevant to the present disclosure.

One problem in the preparation of FVIII compositions is to provide a solution which is suitable for lyophilization and use after subsequent reconstitution. An important criterion in this regard is that the FVIII solution should show a stable FVIII activity and should show no turbidity prior to lyophilization. If an aqueous FVIII solution is turbid prior to lyophilization this is a clear sign that one or more substances in the solution, including FVIII itself, have aggregated. This is highly undesirable, as it is typically an indication of denatured protein, which leads to reduced activity. A second major issue with FVIII formulations is their stability after lyophilization. Signs of poor stability include a reduced remaining activity of FVIII after lyophilization, storage and reconstitution and the presence of high molecular weight complexes of FVIII.

Therefore, there is a great need for compositions comprising FVIII that do not show any turbidity or other relevant impairment of quality like e.g. significant loss of activity before lyophilization and possess long term stability after lyophilization at the same time. As the requirements of a stable solution prior to lyophilization and a stable lyophilisate in terms of composition may differ significantly, both conditions have to be considered when developing such a stable formulation.

It has now been surprisingly discovered that this can be achieved by compositions according to this invention, which comprise histidine and calcium at certain minimum concentrations. The inventors particularly found that, with respect to FVIII stability, a lower concentration of histidine can be balanced by higher calcium concentrations, and vice versa. This is, for example, not disclosed in EP 1 712 223 A1, and, consequently, the compositions described therein do not anticipate the subject matter claimed in the present invention. Specifically, the histidine concentrations of the compositions of EP 1 712 223 A1 are lower than required by claim 1 of the present application. The compositions of the present invention have an additional advantage in that they are close to physiologic conditions in terms of osmolarity. This avoids irritations or other local effects that might be caused by significantly hyper-osmolaric compositions that are present in many prior art formulations of Factor VIII.

SUMMARY OF THE INVENTION

The present invention relates to an aqueous composition of FVIII, which composition may be used to treat a subject with hemophilia A.

The following items (1) to (93) describe various aspects and embodiments of the present invention:

(1) An aqueous composition of coagulation Factor VIII, comprising:
   a. a FVIII molecule;
   b. 40 to 195 mM of a sodium salt;
   c. histidine;
   d. at least 1 mM of a calcium salt; and
   e. a surfactant;
wherein [His]≥180 mM−20*[Ca$^{2+}$], wherein [Ca$^{2+}$] is the concentration of calcium ions in the aqueous composition in millimole per liter, and [His] is the concentration of histidine in the aqueous composition in millimole per liter; and wherein the osmolarity of the composition is 600 mOsmol/L or less.

(2) An aqueous composition of coagulation Factor VIII, comprising:
   a. a FVIII molecule;
   b. 40 to 95 mM of a sodium salt;
   c. histidine;
   d. at least 1 mM of a calcium salt; and
   e. a surfactant;
wherein [His]≥180 mM−20*[Ca$^{2+}$], wherein [Ca$^{2+}$] is the concentration of calcium ions in the aqueous composition in millimole per liter, and [His] is the concentration of histidine in the aqueous composition in millimole per liter, and wherein the osmolarity of the composition is preferably 600 mOsmol/L or less.

(3) An aqueous composition of coagulation Factor VIII, comprising:
   a. a FVIII molecule;
   b. at least 40 mM of a sodium salt;
   c. histidine;
   d. sucrose
   e. at least 1 mM of a calcium salt; and
   f. a surfactant;
wherein [His]≥180 mM−20*[Ca$^{2+}$], wherein [Ca$^{2+}$] is the concentration of calcium ions in the aqueous composition in millimole per liter, and [His] is the concentration of histidine in the aqueous composition in millimole per liter, and wherein the osmolarity of the composition is preferably 600 mOsmol/L or less.

(4) The aqueous composition according to any one of the above, wherein the formulae are subject to the proviso that [His]>0.

(5) The aqueous composition according to item (1) or (3), wherein the concentration of the sodium salt is 50 to 150 mM.

(6) The aqueous composition according to any one of the above, wherein the concentration of the sodium salt is 50 to 95 mM.

(7) The aqueous composition according to any one of the above, wherein the concentration of the sodium salt is 50 to 75 mM.

(8) The aqueous composition according to any one of the above, wherein the concentration of the sodium salt is 60 to 70 mM.

(9) The aqueous composition according to any one of the above, wherein the concentration of the sodium salt is about 65 mM.

(10) The aqueous composition according to any one of the above, wherein the concentration of histidine is at least 5 mM.

(11) The aqueous composition according to any one of the above, wherein the concentration of histidine is at least 10 mM.

(12) The aqueous composition according to any one of the above, wherein the concentration of histidine is at least 20 mM.

(13) The aqueous composition according to any one of the above, wherein the concentration of histidine is at least 30 mM.

(14) The aqueous composition according to any one of the above, wherein the concentration of histidine is at least 40 mM.

(15) The aqueous composition according to any one of the above, wherein the concentration of histidine is at least 50 mM.

(16) The aqueous composition according to any one of the above, wherein the concentration of histidine is 50 to 150 mM.

(17) The aqueous composition according to any one of the above, wherein the concentration of histidine is about 100 mM.

(18) The aqueous composition according to any one of the above, wherein the composition has a pH from 5 to 9.

(19) The aqueous composition according to any one of the above, wherein the composition has a pH from 6 to 8.

(20) The aqueous composition according to any one of the above, wherein the composition has a pH from 6.5 to 7.5.

(21) The aqueous composition according to any one of the above, wherein the composition has a pH from 6.8 to 7.2.

(22) The aqueous composition according to any one of the above, wherein the composition has a pH of about 7.

(23) The aqueous composition according to any one of the above, wherein the composition, upon (i) lyophilization, (ii) storage of the lyophilized composition at a temperature of +25° C. and a relative humidity of 40% for a period of 6 months, and (iii) subsequent reconstitution of the lyophilized composition in distilled water, shows a recovery of FVIII:C activity of at least 80%, relative to the same composition upon (i) lyophilization and, without storage of the lyophilized composition, (ii) subsequent immediate reconstitution in distilled water.

(24) The aqueous composition according to any one of the above, wherein the composition, upon (i) lyophilization, (ii) storage of the lyophilized composition at a temperature of +25° C. and a relative humidity of 40% for a period of 12 months, and (iii) subsequent reconstitution of the lyophilized composition in distilled water, shows a recovery of FVIII:C activity of at least 80%, relative to the same composition upon (i) lyophilization and, without storage of the lyophilized composition, (ii) subsequent immediate reconstitution in distilled water.

(25) The aqueous composition according to any one of the above, wherein the composition, upon (i) lyophilization, (ii) storage of the lyophilized composition at a temperature of +25° C. and a relative humidity of 40% for a period of 18 months, and (iii) subsequent reconstitution of the lyophilized composition in distilled water, shows a recovery of FVIII:C activity of at least 80%, relative to the same composition upon (i) lyophilization and, without storage of the lyophilized composition, (ii) subsequent immediate reconstitution in distilled water.

(26) The aqueous composition according to any one of the above, wherein the composition, upon (i) lyophilization, (ii) storage of the lyophilized composition at a temperature of +25° C. and a relative humidity of 40% for a period of 24 months, and (iii) subsequent reconstitution of the lyophilized composition in distilled water, shows a recovery of FVIII:C activity of at least 80%, relative to the same composition upon (i) lyophilization and, without storage of the lyophilized composition, (ii) subsequent immediate reconstitution in distilled water.

(27) The aqueous composition according to any one of the above, wherein the composition, upon (i) lyophilization, (ii)

storage of the lyophilized composition at a temperature of +25° C. and a relative humidity of 40% for a period of 36 months, and (iii) subsequent reconstitution of the lyophilized composition in distilled water, shows a recovery of FVIII:C activity of at least 80%, relative to the same composition upon (i) lyophilization and, without storage of the lyophilized composition, (ii) subsequent immediate reconstitution in distilled water.

(28) The aqueous composition according to any one of the above, wherein the composition, upon (i) lyophilization, (ii) storage of the lyophilized composition at a temperature of +40° C. and a relative humidity of 60% for a period of 6 months, and (iii) subsequent reconstitution of the lyophilized composition in distilled water, shows a recovery of FVIII:C activity of at least 80%, relative to the same composition upon (i) lyophilization and, without storage of the lyophilized composition, (ii) subsequent immediate reconstitution in distilled water.

(29) The aqueous composition according to any one of the above, wherein the composition, upon (i) lyophilization, (ii) storage of the lyophilized composition at a temperature of +40° C. and a relative humidity of 60% for a period of 12 months, and (iii) subsequent reconstitution of the lyophilized composition in distilled water, shows a recovery of FVIII:C activity of at least 80%, relative to the same composition upon (i) lyophilization and, without storage of the lyophilized composition, (ii) subsequent immediate reconstitution in distilled water.

(30) The aqueous composition according to any one of the above, wherein the composition, upon (i) lyophilization, (ii) storage of the lyophilized composition at a temperature of +40° C. and a relative humidity of 60% for a period of 18 months, and (iii) subsequent reconstitution of the lyophilized composition in distilled water, shows a recovery of FVIII:C activity of at least 80%, relative to the same composition upon (i) lyophilization and, without storage of the lyophilized composition, (ii) subsequent immediate reconstitution in distilled water.

(31) The aqueous composition according to any one of the above, wherein the composition, upon (i) lyophilization, (ii) storage of the lyophilized composition at a temperature of +40° C. and a relative humidity of 60% for a period of 24 months, and (iii) subsequent reconstitution of the lyophilized composition in distilled water, shows a recovery of FVIII:C activity of at least 80%, relative to the same composition upon (i) lyophilization and, without storage of the lyophilized composition, (ii) subsequent immediate reconstitution in distilled water.

(32) The aqueous composition according to any one of the above, wherein the composition, upon (i) lyophilization, (ii) storage of the lyophilized composition at a temperature of +25° C. and a relative humidity of 40% for a period of 12 months, and (iii) subsequent reconstitution of the lyophilized composition in distilled water, has a turbidity of 18 NTU or less.

(33) The aqueous composition according to any one of the above, wherein the calcium salt is calcium chloride.

(34) The aqueous composition according to any one of the above, wherein the sodium salt is sodium chloride.

(35) The aqueous composition according to any one of the above, wherein the composition further comprises a carbohydrate.

(36) The aqueous composition according to above (35), wherein the carbohydrate is selected from the group consisting of sucrose, trehalose and raffinose.

(37) The aqueous composition according to above (35) or (36), wherein the carbohydrate is sucrose.

(38) The aqueous composition according to any one of above (35) to (37), wherein the concentration of the carbohydrate is 1 to 20% w/w.

(39) The aqueous composition according to any one of above (35) to (37), wherein the concentration of the carbohydrate is 2 to 10% w/w.

(40) The aqueous composition according to any one of above (35) to (37), wherein the concentration of the carbohydrate is 3 to 8% w/w.

(41) The aqueous composition according to any one of above (35) to (37), wherein the concentration of the carbohydrate is 4 to 6% w/w.

(42) The aqueous composition according to any one of above (35) to (37), wherein the concentration of the carbohydrate is about 5% w/w.

(43) The aqueous composition according to any one of the above, wherein the concentration of the surfactant is at least 0.001% v/v.

(44) The aqueous composition according to any one of the above, wherein the concentration of the surfactant is 0.001 to 0.1% v/v.

(45) The aqueous composition according to any one of the above, wherein the concentration of the surfactant is 0.002 to 0.2% v/v.

(46) The aqueous composition according to any one of the above, wherein the concentration of the surfactant is 0.005% v/v.

(47) The aqueous composition according to any one of the above, wherein the surfactant is a non-naturally occurring surfactant.

(48) The aqueous composition according to any one of the above, wherein the surfactant is polysorbate 80.

(49) The aqueous composition according to any one of the above, wherein the surfactant is polysorbate 20.

(50) The aqueous composition according to any one of the above, wherein the composition further comprises at least one amino acid other than histidine.

(51) The aqueous composition according to above (50), wherein the at least one amino acid other than histidine is selected from the group consisting of arginine, asparagine, aspartic acid, glutamic acid, glutamine, lysine, methionine, phenylalanine, leucine, isoleucine and combinations thereof.

(52) The aqueous composition according to above (50), wherein the at least one amino acid other than histidine is arginine.

(53) The aqueous composition according to above (50), wherein the at least one amino acid other than histidine is asparagine.

(54) The aqueous composition according to above (50), wherein the at least one amino acid other than histidine is aspartic acid.

(55) The aqueous composition according to above (50), wherein the at least one amino acid other than histidine is glutamic acid.

(56) The aqueous composition according to above (50), wherein the at least one amino acid other than histidine is glutamine.

(57) The aqueous composition according to above (50), wherein the at least one amino acid other than histidine is lysine.

(58) The aqueous composition according to above (50), wherein the at least one amino acid other than histidine is methionine.

(59) The aqueous composition according to above (50), wherein the at least one amino acid other than histidine is phenylalanine.

(60) The aqueous composition according to above (50), wherein the at least one amino acid other than histidine is isoleucine.

(61) The aqueous composition according to any one of the above (50) to (60), wherein the concentration of the at least one amino acid other than histidine is at least 0.1 mM.

(62) The aqueous composition according to any one of the above (50) to (60), wherein the concentration of the at least one amino acid other than histidine is at least 1 mM.

(63) The aqueous composition according to any one of the above (50) to (60), wherein the concentration of the at least one amino acid other than histidine is 5 to 300 mM.

(64) The aqueous composition according to any one of the above (50) to (60), wherein the concentration of the at least one amino acid other than histidine is 10 to 200 mM.

(65) The aqueous composition according to any one of the above, wherein the composition further comprises at least one antioxidant.

(66) The aqueous composition according to above (65), wherein the at least one antioxidant is selected from the group consisting of reduced glutathione, methionine, cysteine, sodium sulfite, vitamin A, vitamin E, ascorbic acid, sodium ascorbate and combinations thereof.

(67) The aqueous composition according to above (65), wherein the at least one antioxidant is reduced glutathione.

(68) The aqueous composition according to above (65), wherein the at least one antioxidant is methionine.

(69) The aqueous composition according to above (65), wherein the at least one antioxidant is cysteine.

(70) The aqueous composition according to above (65), wherein the at least one antioxidant is sodium sulfite.

(71) The aqueous composition according to above (65), wherein the at least one antioxidant is vitamin A.

(72) The aqueous composition according to above (65), wherein the at least one antioxidant is vitamin E.

(73) The aqueous composition according to above (65), wherein the at least one antioxidant is ascorbic acid.

(74) The aqueous composition according to above (65), wherein the at least one antioxidant is sodium ascorbate.

(75) The aqueous composition according to any one of the above (65) to (74), wherein the concentration of the at least one antioxidant is at least 0.05 mM.

(76) The aqueous composition according to any one of the above (65) to (74), wherein the concentration of the at least one antioxidant is 0.05 to 100 mM.

(77) The aqueous composition according to any one of the above (65) to (74), wherein the concentration of the at least one antioxidant is 0.1 to 20 mM.

(78) The aqueous composition according to any one of the above (65) to (74), wherein the concentration of the at least one antioxidant is 0.25 to 5 mM.

(79) The aqueous composition according to any one of the above, wherein the Factor VIII molecule is a non-naturally occurring FVIII molecule.

(80) The aqueous composition according to (79), wherein the Factor VIII molecule has been recombinantly produced.

(81) The aqueous composition according to (79) or (80), wherein the Factor VIII molecule has a glycosylation pattern different from that of human plasma-derived FVIII.

(82) The aqueous composition according to an one of the above (79) to (81), wherein the FVIII molecule has an amino acid sequence different from SEQ ID NO:1.

(83) The aqueous composition according to an one of the above (79) to (82), wherein the FVIII molecule is selected from the group consisting of (i) B-domain deleted or truncated FVIII molecules, (ii) single-chain FVIII molecules, (iii) FVIII molecules having protective groups or half-life extending moieties, (iv) fusion proteins comprising a FVIII amino acid sequence fused to a heterologous amino acid sequence, and (v) combinations thereof.

(84) The aqueous composition according to any one of the above, wherein the Factor VIII molecule has the amino acid sequence as shown in SEQ ID NO:2.

(85) The aqueous composition according to any one of the above, wherein the composition has a turbidity of 18 NTU or less, preferably of 6 NTU or less, more preferably of 3 NTU or less.

(86) The aqueous composition according to the above (85), wherein the composition, prior to lyophilization, has a turbidity of 18 NTU or less, preferably of 6 NTU or less, more preferably of 3 NTU or less.

(87) The aqueous composition according to the above (85), wherein the composition, upon lyophilization and reconstitution in distilled water, has a turbidity of 18 NTU or less, preferably of 6 NTU or less, more preferably of 3 NTU or less.

(88) A composition obtainable by lyophilizing the aqueous composition according to any one of the above.

(89) An aqueous composition obtainable by reconstituting the lyophilized aqueous composition according to above (88) with an aqueous solution.

(90) The aqueous composition of (89), wherein the aqueous solution is selected from distilled water, a salt solution and a solution comprising histidine.

(91) A method of stabilizing a FVIII molecule, comprising mixing the components defined in any one of the above (1) to (3) to obtain an aqueous composition, and lyophilizing the aqueous composition.

(92) The method of (91), wherein the aqueous composition obtained is a composition according to any one of the above (1) to (87).

(93) A method of treating a blood coagulation disorder, comprising administering to a subject a pharmaceutically effective amount of the composition of the above (89) or (90).

BRIEF DESCRIPTION OF DRAWINGS

FIG. 1 depicts the relationship between the concentrations of histidine and calcium ions in the composition of the present invention. The FIGURE summarizes the results of a liquid formulation study (Example 7) with varying histidine and calcium chloride concentrations whereas the other excipients were kept constant (65 mmol/L sodium chloride, 5% sucrose, 0.005% Tween® 80). Dots represent a turbidity above a threshold level of 18 NTU, diamonds represent a clear solution (turbidity less than or equal to 18 NTU). The graph illustrates that if certain concentrations of histidine and calcium ions are applied, a clear solution is resulting. The requirement for a clear solution is represented by a formula given later.

DETAILED DESCRIPTION OF INVENTION

Factor VIII Molecules

As used herein, the term "Factor VIII" or "FVIII" refers to molecules having at least part of the coagulation activity of human native Factor VIII. Human FVIII consists of 2351 amino acids (including a signal peptide) and 2332 amino acids (without the signal peptide). "Human native FVIII" is the human plasma-derived FVIII molecule having the full length sequence as shown in SEQ ID NO: 1 (amino acid 1-2332). The detailed domain structure, A1-a1-A2-a2-B-a3-A3-C1-C2 has the corresponding amino acid residues (referring to SEQ ID NO 1): A1 (1-336), a1 (337-372), A2 (373-710), a2 (711-740), B (741-1648), a3 (1649-1689), A3 (1690-2020), C1 (2021-2173) and C2 (2174-2332).

The coagulation activity of the FVIII molecule can be determined using a one-stage clotting assay (e.g. as described in Lee et al., Thrombosis Research 30, 511 519 (1983)) or a chromogenic substrate assay (e.g. the coamatic FVIII test kit from Chromogenix-Instrumentation Laboratory SpA V. le Monza 338-20128 Milano, Italy). Further details of these activity assays are described infra.

Preferably, the FVIII molecules used in accordance with this invention have at least 10% of the specific molar activity of human native FVIII. The term "specific molar activity" refers to the coagulation activity per mole of FVIII and is indicated in "IU/mole FVIII.

In a preferred embodiment, the FVIII molecule is a non-naturally occurring FVIII molecule. Preferably, the non-naturally occurring FVIII molecule has been produced recombinantly. In another embodiment, the FVIII molecule has been produced in cell culture. In another preferred embodiment, the non-naturally occurring FVIII molecule has a glycosylation pattern different from that of plasma-derived FVIII. In yet another embodiment, the FVIII molecule is selected from the group consisting of (i) B-domain deleted or truncated FVIII molecules, (ii) single-chain FVIII molecules, (iii) recombinantly produced two-chain FVIII molecules, (iv) FVIII molecules having protective groups or half-life extending moieties, (v) fusion proteins comprising a FVIII amino acid sequence fused to a heterologous amino acid sequence, and (vi) combinations thereof.

The terms "Factor VIII" and "FVIII" are used synonymously herein. "Factor VIII compositions" in the sense of the present invention include compositions comprising FVIII and FVIIIa. FVIIIa may typically be present in small amounts, e.g. about 1 to 2% FVIIIa, referred to the total amount of FVIII protein in the composition. "FVIII" includes natural allelic variations of FVIII that may exist and occur from one individual to another. FVIII may be plasma-derived or recombinantly produced, using well known methods of production and purification. The degree and location of glycosylation, tyrosine sulfation and other post-translation modifications may vary, depending on the chosen host cell and its growth conditions.

The term FVIII includes FVIII analogues. The term "FVIII analogue" as used herein refers to a FVIII molecule (full-length or B-domain-truncated/deleted) wherein one or more amino acids have been substituted or deleted compared to SEQ ID NO 1 or, for B-domain truncated/deleted FVII molecules, the corresponding part of SEQ ID NO 1. FVIII analogues do not occur in nature but are obtained by human manipulation.

The Factor VIII molecules included in the compositions of the present invention may also be B-domain-truncated/deleted FVIII molecules wherein the remaining domains correspond to the sequences as set forth in amino acid numbers 1-740 and 1649-2332 of SEQ ID NO: 1. Other forms of B-domain deleted FVIII molecules have additionally a partial deletion in their a3 domain, which leads to single-chain FVIII molecules.

It follows that these FVIII molecules are recombinant molecules produced in transformed host cells, preferably of mammalian origin. However, the remaining domains in a B-domain deleted FVIII, (i.e. the three A-domains, the two C-domains and the a1, a2 and a3 regions) may differ slightly e.g. about 1%, 2%, 3%, 4% or 5% from the respective amino acid sequence as set forth in SEQ ID NO 1 (amino acids 1-740 and 1649-2332).

The FVIII molecules included in the composition of the present invention may be two-chain FVIII molecules or single-chain FVIII molecules. The FVIII molecules included in the composition of the present invention may also be biologically active fragments of FVIII, i.e., FVIII wherein domain(s) other than the B-domain has/have been deleted or truncated, but wherein the FVIII molecule in the deleted/truncated form retains its ability to support the formation of a blood clot. FVIII activity can be assessed in vitro using techniques well known in the art. A preferred test for determining FVIII activity according to this invention is the chromogenic substrate assay or the one stage assay (see infra). Amino acid modifications (substitutions, deletions, etc.) may be introduced in the remaining domains, e.g., in order to modify the binding capacity of Factor VIII with various other components such as e.g. Von Willebrand Factor (vWF), low density lipoprotein receptor-related protein (LPR), various receptors, other coagulation factors, cell surfaces, etc. or in order to introduce and/or abolish glycosylation sites, etc. Other mutations that do not abolish FVIII activity may also be accommodated in a FVIII molecule/analogue for use in a composition of the present invention.

FVIII analogues also include FVIII molecules, in which one or more of the amino acid residues of the parent polypeptide have been deleted or substituted with other amino acid residues, and/or wherein additional amino acid residues has been added to the parent FVIII polypeptide.

Furthermore, the Factor VIII molecules/analogues may comprise other modifications in e.g. the truncated B-domain and/or in one or more of the other domains of the molecules ("FVIII derivatives"). These other modifications may be in the form of various molecules conjugated to the Factor VIII molecule, such as e.g. polymeric compounds, peptidic compounds, fatty acid derived compounds, etc.

The term FVIII includes glycopegylated FVIII. In the present context, the term "glycopegylated FVIII" is intended to designate a Factor VIII molecule (including full length FVIII and B-domain truncated/deleted FVIII) wherein one or more PEG group(s) has/have been attached to the FVIII polypeptide via the polysaccharide sidechain(s) (glycan(s)) of the polypeptide.

The term FVIII includes FVIII molecules having protective groups or half-life extending moieties. The terms "protective groups"/"half-life extending moieties" is herein understood to refer to one or more chemical groups attached to one or more amino acid site chain functionalities such as —SH, —OH, —COOH, —CONH2, —NH2, or one or more N- and/or O-glycan structures and that can increase in vivo circulatory half-life of a number of therapeutic proteins/peptides when conjugated to these proteins/peptides. Examples of protective groups/half-life extending moieties include: Biocompatible fatty acids and derivatives thereof, Hydroxy Alkyl Starch (HAS) e.g. Hydroxy Ethyl Starch (HES), Poly (Gly$_x$-Ser$_y$)$_n$ (Homo Amino acid Polymer (HAP)), Hyaluronic acid (HA), Heparosan polymers (HEP), Phosphorylcholine-based polymers (PC polymer), Fleximer® polymers (Mersana Therapeutics, Mass., USA), Dextran, Poly-sialic acids (PSA), polyethylene glycol (PEG), an Fc domain, Transferrin, Albumin, Elastin like peptides, XTEN® polymers (Amunix, Calif., USA), Albumin binding peptides, a von Willebrand factor fragment (vWF fragment), a Carboxyl Terminal Peptide (CTP peptide, Prolor Biotech, Ill.), and any combination thereof (see, for example, McCormick, C. L., A. B. Lowe, and N. Ayres, Water-Soluble Polymers, in Encyclopedia of Polymer Science and Technology. 2002, John Wiley & Sons, Inc.). The manner of derivatization is not critical and can be elucidated from the above.

The FVIII molecules which can be used in accordance with this invention include fusion proteins comprising a FVIII amino acid sequence fused to a heterologous amino acid sequence, preferably a half-life extending amino acid sequence. Preferred fusion proteins are Fc fusion proteins and albumin fusion proteins. The term "Fc fusion protein" is herein meant to encompass FVIII fused to an Fc domain that can be derived from any antibody isotype. An IgG Fc domain will often be preferred due to the relatively long circulatory half-life of IgG antibodies. The Fc domain may furthermore be modified in order to modulate certain effector functions such as e.g. complement binding and/or binding to certain Fc receptors. Fusion of FVIII with an Fc domain, which has the capacity to bind to FcRn receptors, will generally result in a prolonged circulatory half-life of the fusion protein compared to the half-life of the wt FVIII. It follows that a FVIII molecule for use in the present invention may also be a derivative of a FVIII analogue, such as, for example, a fusion protein of an FVIII analogue, a PEGylated or glycoPEGylated FVIII analogue, or a FVIII analogue conjugated to a heparosan polymer. The term "albumin fusion protein" is herein meant to encompass FVIII fused to an albumin amino acid sequence or a fragment or derivative thereof. The heterologous amino acid sequence may be fused to the N- or C-terminus of FVIII, or it may be inserted internally within the FVIII amino acid sequence. The heterologous amino acid sequence may be any "half life extending polypeptide" described in WO 2008/077616 A1, the disclosure of which is incorporated herein by reference.

Examples of FVIII molecules for use in compositions of the present invention comprise for instance the FVIII molecules described in WO 2010/045568, WO 2009/062100, WO 2010/014708, WO 2008/082669, WO 2007/126808, US 2010/0173831, US 2010/0173830, US 2010/0168391, US 2010/0113365, US 2010/0113364, WO 2003/031464, WO 2009/108806, WO 2010/102886, WO 2010/115866, WO 2011/101242, WO 2011/101284, WO 2011/101277, WO 2011/131510, WO 2012/007324, WO 2011/101267, WO 2013/083858, and WO 2004/067566.

Examples of FVIII molecules, which can be used in a composition of the present invention include the active ingredient of Advate®, Helixate®, Kogenate®, Xyntha® as well as the FVIII molecule described in WO 2008/135501, WO 2009/007451 and the construct designated "dBN(64-53)" of WO 2004/067566. This construct has the amino acid sequence shown in SEQ ID NO 2.

The concentration of Factor VIII in the composition of the present invention is typically in the range of 10-10,000 IU/mL. In different embodiments, the concentration of FVIII molecules in the compositions of the invention is in the range of 10-8,000 IU/mL, or 10-5,000 IU/mL, or 20-3,000 IU/mL, or 50-1,500 IU/mL, or 3,000 IU/mL, or 2,500 IU/mL, or 2,000 IU/mL, or 1,500 IU/mL, or 1,200 IU/mL, 1,000 IU/mL, or 800 IU/mL, or 600 IU/mL, or 500 IU/mL, or 400 IU/mL, or 300 IU/mL, or 250 IU/mL, or 200 IU/mL, or 150 IU/mL, or 100 IU/mL.

"International Unit," or "IU," is a unit of measurement of the blood coagulation activity (potency) of FVIII as measured by a FVIII activity assay such as a one stage clotting assay or a chromogenic substrate FVIII activity assay using a standard calibrated against an international standard preparation calibrated in "IU". One stage clotting assays are known to the art, such as that described in N Lee, Martin L, et al., An Effect of Predilution on Potency Assays of FVIII Concentrates, Thrombosis Research (Pergamon Press Ltd.) 30, 511 519 (1983). Principle of the one stage assay: The test is executed as a modified version of the activated Partial Thromboplastin Time (aPTT)-assay: Incubation of plasma with phospholipids and a surface activator leads to the activation of factors of the intrinsic coagulation system. Addition of calcium ions triggers the coagulation cascade. The time to formation of a measurable fibrin clot is determined. The assay is executed in the presence of Factor VIII deficient plasma. The coagulation capability of the deficient plasma is restored by Coagulation Factor VIII included in the sample to be tested. The shortening of coagulation time is proportional to the amount of Factor VIII present in the sample. The activity of Coagulation Factor VIII is quantified by direct comparison to a standard preparation with a known activity of Factor VIII in International Units.

Another standard assay is a chromogenic substrate assay. Chromogenic substrate assays may be purchased commercially, such as the coamatic FVIII test kit (Chromogenix-Instrumentation Laboratory SpA V. le Monza 338-20128 Milano, Italy). Principle of the chromogenic assay: In the presence of calcium and phospholipid, Factor X is activated by Factor IXa to Factor Xa. This reaction is stimulated by Factor VIIIa as cofactor. FVIIIa is formed by low amounts of thrombin in the reaction mixture from FVIII in the sample to be measured. When using the optimum concentrations of $Ca^{2+}$, phospholipid and Factor IXa and an excess quantity of Factor X, activation of Factor X is proportional to the potency of Factor VIII. Activated Factor X releases the chromophore pNA from the chromogenic substrate S-2765. The release of pNA, measured at 405 nm, is therefore proportional to the amount of FXa formed, and, therefore, also to the Factor VIII activity of the sample.

Freeze-drying or lyophilization, unless otherwise indicated by the context in which it appears, shall be used to denote a drying process in which a solution of materials (i.e. an active pharmaceutical ingredient and various formulation additives or "excipients") is converted into a solid. A typical freeze-drying process consists of three stages, "freezing", "primary drying" and "secondary drying". In the freezing stage almost all contained water is converted into ice and solutes into solids (crystalline or amorphous). In the primary drying stage the ice is removed from the product by direct sublimation which is achieved by maintaining a favorable pressure gradient between the water molecules (ice) and the surrounding atmosphere. In the secondary drying stage residual moisture is removed from the product by desorption.

If concentrations (w/v) are given for freeze-dried compositions they refer to the volume directly prior to freeze-drying.

Unless otherwise noted, percentage terms express weight/weight percentages and temperatures are in the Celsius scale.

Osmolarity

The Factor VIII composition of the present invention typically has an osmolarity of less than 0.6 Osm/L. This is closer to physiological conditions than the osmolarities in many prior art formulations that contain high concentrations of sodium chloride. In different embodiments of the invention, the formulation has an osmolarity of below 0.55 Osm/L, below 0.5 Osm/L, below 0.45 Osm/L, or below 0.4 Osm/L. The terms "osmolarity" and "osmotic concentration" are used interchangeably herein.

Osmolarity, or osmotic concentration, is the measure of solute concentration, defined as the number of osmoles (Osm) of solute per liter (L) of solution (osmol/L or Osm/L). Whereas molarity measures the number of moles of solute per unit volume of solution, osmolarity measures the number of osmoles of solute particles per unit volume of solution.

The theoretical calculation of osmolarity is well known to the person skilled in the art. Briefly, one calculates for each component of the solution the product of the osmotic coefficient f, the number of particles n into which the molecule dissociates in water, and the molar concentration, and sums the result over all components. The osmolarity of a solution can be calculated from the following expression: $Osm/L = \Sigma_i f_i n_i C_i$, where the index i represents the identity of a particular component; f, is the osmotic coefficient for a particular component; n is the number of particles into which the molecule dissociates in water; C is the molar concentration of the component. The molar concentration has some temperature dependence; for the present purpose it is referred to the concentrations at 25° C.

An alternative way to assess the osmotic pressure that a solution may exert after injection is by evaluating the osmolality, in which the content of the components is evaluated relative to solvent mass. Osmolality and osmolarity can easily be interconverted if the density of the solution and the dry mass of the dissolved components are known. Osmolality can be measured by a number of methods, most commonly freezing point depression.

For example, for water, 1 Osmol of a solute added to 1 kg of water lowers the freezing point by 1.86° C. Methods for measuring the osmolality of a solution by freezing point depression are described, for example, in the European Pharmacopeia 2.2.35 and the U.S. Pharmacopeia chapter 785.

The table below lists the osmotic coefficients and number of particles n for some important excipients. For other components, a value of f=1 provides a sufficiently good approximation for practical purposes, and the value of n is well known for essentially all compounds relevant for pharmaceutical preparations for parenteral use.

| Excipient | f | n |
| --- | --- | --- |
| NaCl | 0.93 | 2 |
| CaCl$_2$ | 0.86 | 3 |
| Sucrose | 1.02 | 1 |
| Histidine | 1.0 | 1 |
| L-Methionine | 1.0 | 1 |
| Poloxamer-188 | 1.0 | 1 |
| Polysorbate 20 | 1.0 | 1 |
| Polysorbate 80 | 1.0 | 1 |

Salts

The composition according to the present invention comprises a sodium salt.

In one embodiment the composition of the present invention contains at least 40 mM of a sodium salt (e.g. NaCl). In a series of embodiments, the composition comprises 40 to 195 mM of a sodium salt (e.g. NaCl), or 45 to 180 mM, or 45 to 150 mM, or 50 to 125 mM or 50 to 100 mM, or 60 to 95 mM, or 60 to 75 mM, e.g. about 65 mM. In yet another embodiment the concentration of sodium salt (e.g. NaCl) is 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95 mM.

Preferably, the sodium salt is sodium chloride; in another embodiment, the salt is sodium acetate. In a third embodiment, the composition of the invention contains a mixture of sodium chloride and sodium acetate.

The composition according to the present invention further comprises a calcium salt. The calcium salt used in accordance with the present invention is typically soluble in water so that it dissociates into one or more calcium ions and counter-anions upon dissolution in an aqueous solution. The term "$Ca^{2+}$" is synonymous to the term "calcium ion".

In one embodiment the calcium concentration is defined by the following formula, wherein $[Ca^{2+}]$ is the concentration of calcium ions in millimole per liter, and [His] is the concentration of histidine in millimole per liter:

$[Ca^{2+}] \geq 9$ mM$-0.05*$[His]

In another embodiment the calcium concentration is defined by the following formula, wherein $[Ca^{2+}]$ is the concentration of calcium ions in millimole per liter, and [His] is the concentration of histidine in millimole per liter:

$[Ca^{2+}] \geq 9.5$ mM$-0.05*$[His]

In another embodiment the calcium concentration is defined by the following formula, wherein $[Ca^{2+}]$ is the concentration of calcium ions in millimole per liter, and [His] is the concentration of histidine in millimole per liter:

$[Ca^{2+}] \geq 10$ mM$-0.05*$[His]

In another embodiment the calcium concentration is defined by the following formula, wherein $[Ca^{2+}]$ is the concentration of calcium ions in millimole per liter, and [His] is the concentration of histidine in millimole per liter:

$[Ca^{2+}] > 10.5$ mM$-0.05*$[His]

The above formulae are subject to the proviso that $[Ca^{2+}] > 0$. Typically, the composition contains at least 1 mM, preferably at least 2 mM, more preferably at least 4 mM, most preferably at least 5 mM of a calcium salt. In another embodiment the composition contains up to 100 mM of a calcium salt. In another embodiment, the composition comprises 1-50 mM of a calcium salt, or 2-40 mM, or 3-30 mM, or 4-20 mM. In one particular embodiment, the composition contains about 10 mM of a calcium salt.

The calcium salt may, for example, be selected from the group of calcium chloride, calcium acetate, calcium gluconate, calcium lactate, calcium benzoate and mixtures thereof, and other soluble calcium salts well known by the person skilled in the art. In a preferred embodiment, the calcium salt is calcium chloride.

Histidine

The composition according to the present invention comprises histidine, preferably L-histidine.

In one embodiment the histidine concentration is defined by the following formula, wherein $[Ca^{2+}]$ is the concentration of calcium ions in millimole per liter, and [His] is the concentration of histidine in millimole per liter:

$[His] \geq 180$ mM$-20*[Ca^{2+}]$

In another embodiment the histidine concentration is defined by the following formula, wherein $[Ca^{2+}]$ is the concentration of calcium ions in millimole per liter, and [His] is the concentration of histidine in millimole per liter:

$[His] \geq 190$ mM$-20*[Ca^{2+}]$

In another embodiment the histidine concentration is defined by the following formula, wherein $[Ca^{2+}]$ is the concentration of calcium ions in millimole per liter, and [His] is the concentration of histidine in millimole per liter:

$[His] \geq 200$ mM$-20*[Ca^{2+}]$

In another embodiment the histidine concentration is defined by the following formula, wherein $[Ca^{2+}]$ is the concentration of calcium ions in millimole per liter, and [His] is the concentration of histidine in millimole per liter:

$$[His] \geq 210 \text{ mM} - 20*[Ca^{2+}]$$

The above formulae are subject to the proviso that [His]>0. Typically, the concentration of histidine is at least 5 mM, preferably at least 10 mM, preferably at least 20 mM, preferably 20-400 mM, preferably at least 25 mM, preferably 25-200 mM, preferably at least 50 mM, preferably 50-300 mM, preferably 55-170 mM, preferably 60-150 mM, preferably 65-120 mM, more preferably 50-100 mM, e.g. about 100 mM. In yet another embodiment the concentration of histidine is 10, 20, 25, 30, 35, 40, 45, 50, 55, 60, 65, 70, 75, 80, 85, 90, 95, 100, 105, 110, 115, 120, 130, 140, 150, 160, 170, 180, 190, 200, 300 or 400 mM.

Surfactant

The composition according to the present invention comprises a surfactant. As used herein, "surfactants" refers to agents which protect the active substance from air-to-solution interface or solution-to-surface interface induced stress or damage. Preferably, the surfactant is a non-naturally occurring surfactant.

Typical non-naturally occurring surfactants (with examples of trade names given in brackets [ ]) are polyoxyethylene sorbitan fatty acid esters such as polyoxyethylene (20) sorbitan monolaurate [Tween® 20], polyoxyethylene (20) sorbitan monopalmitate [Tween® 40] or polyoxyethylene (20) sorbitan monooleate [Tween® 80], poloxamers such as polyoxypropylene-polyoxyethylene block copolymer [Pluronic® F68/poloxamer 188], polyethylene glycol octylphenyl ether [Triton® X-100] or polyoxyethyleneglycol dodecyl ether [Brij® 35]. The use of a surfactant in aqueous compositions is well-known to the skilled person. For convenience reference is made to Remington: The Science and Practice of Pharmacy, 19th edition, 1995. In one embodiment of the invention, the composition comprises sorbitan monooleate [Tween® 80]. In certain embodiments, the composition of the present invention comprises a surfactant which is not sensitive to oxidation, e.g. alkyl saccharides. In another embodiment, the surfactant is a vegetable-derived surfactant, and/or it is free from petrochemicals, and/or it has been produced without using petrochemicals.

In one embodiment, the concentration of the surfactant is at least 0.001% v/v, preferably 0.001-0.1% v/v, preferably 0.002-0.3% v/v, more preferably 0.003 to 0.1% v/v, and most preferably about 0.005% v/v. In yet another embodiment the concentration of the surfactant is 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.5, 0.7, 0.8, 0.9 or 1.0% v/v. In one embodiment, the concentration of Polyoxyethylene (20) sorbitan monooleate [Tween® 80] is at least 0.001% v/v, preferably 0.001-0.1% v/v, preferably 0.002-0.3% v/v, more preferably 0.003 to 0.1% v/v, and most preferably about 0.005% v/v.

Buffer

The composition according to the invention may comprise a buffering agent. As used herein, "buffering agents" or "buffers" refers to agents which maintain the pH of the preparation in a range where administration of the preparation (e.g. intravenous or subcutaneous) is normally well tolerated (e.g. pH 5 to 9) and, furthermore, avoid pH shifts and protect the active substance from pH induced stress or damage during lyophilization. Typical examples for substances used as buffer substances are e.g. carbonate, phosphate, citrate, borate, 2-amino-2-hydroxymethyl-1,-3-propanediol[=TRIS], histidine, glycine.

The buffer (or buffering agents) may be selected from the group consisting of acetate, benzoate, carbonate, citrate, glycylglycine, Hepes, histidine, glycine, and TRIS, bicine, tricine, succinate, aspartic acid, glutamic acid or mixtures thereof. In one embodiment of the invention, the concentration of the buffering substance is 1 to 200 mM, such as, e.g., 1 to 150 mM or 1 to 50 mM or 1 to 25 mM or 5 to 20 mM or 5 to 15 mM.

The composition of the invention typically has a pH from 4 to 10. In another embodiment, the composition has a pH of 5.0 to 9.0 or 6.0 to 8.0 or 6.5 to 7.5 or 6.8 to 7.2 or about 7. In other embodiments, the pH of the composition is 5.5±0.2, 5.6±0.2, 5.7±0.2, 5.8±0.2, 5.9±0.2, 6.0±0.2, 6.1±0.2, 6.2±0.2, 6.3±0.2, 6.4±0.2, 6.5±0.2, 6.6±0.2, 6.7±0.2, 6.8±0.2, 6.9±0.2, 7.0±0.2, 7.1±0.2, 7.2±0.2, 7.3±0.2, 7.4±0.2, or 7.5±0.2. In other embodiments, the pH of the composition is 5.5±0.1, 5.6±0.1, 5.7±0.1, 5.8±0.1, 5.9±0.1, 6.0±0.1, 6.1±0.1, 6.2±0.1, 6.3±0.1, 6.4±0.1, 6.5±0.1, 6.6±0.1, 6.7±0.1, 6.8±0.1, 6.9±0.1, 7.0±0.1, 7.1±0.1, 7.2±0.1, 7.3±0.1, 7.4±0.1, or 7.5±0.1. In yet other embodiments, the pH of the stabilizing formulation is 5.5, 5.6, 5.7, 5.8, 5.9, 6.0, 6.1, 6.2, 6.3, 6.4, 6.5, 6.6, 6.7, 6.8, 06.9, 7.0, 7.1, 7.2, 7.3, 7.4, 7.5, 7.6, 7.7, 7.8, 7.9, or 8.0.

Carbohydrates

The composition of the invention may further comprise a carbohydrate. As used herein, "carbohydrates" refers to sugars, such as mono-, di-, or polysaccharides, or water-soluble glucans, including for example fructose, glucose, mannose, mannitol, sorbose, sorbit, xylose, maltose, lactose, sucrose, galactose, dextran, trehalose, pullulan, dextrin, cyclodextrin, soluble starch, hydroxyethyl starch, and carboxymethylcellulose may be used.

The carbohydrate may, for example, be selected from the group of mono-, di-, or polysaccharides (including for example the monosaccharides fructose, glucose, mannose, galactose, the disaccharides lactose, sucrose, trehalose, maltose and the polysaccharides dextran, raffinose, stachyose).

In one embodiment of the invention, the FVIII composition comprises one or more carbohydrates from the group of: sucrose, raffinose, trehalose, or mixtures thereof. In one embodiment, the FVIII composition comprises a carbohydrate in a concentration of 2 to 10% w/w, preferably 3 to 8% w/w, preferably 4 to 6% w/w and most preferably 5% w/w. In yet another embodiment the concentration of the carbohydrate is 2, 3, 4, 5, 6, 7, 8, 9 or 10% w/w.

In specific embodiments the carbohydrate is sucrose. In one embodiment, the FVIII composition comprises sucrose in a concentration of 2-10% w/w, preferably 3-8% w/w, preferably 4-6% w/w and most preferably 5% w/w. In yet another embodiment the concentration of sucrose is 2, 3, 4, 5, 6, 7, 8, 9 or 10% w/w.

In specific embodiments the carbohydrate is trehalose. In one embodiment, the FVIII composition comprises trehalose in a concentration of 2 to 10% w/w, preferably 3 to 8% w/w, preferably 4 to 6% w/w and most preferably 5% w/w. In yet another embodiment the concentration of trehalose is 2, 3, 4, 5, 6, 7, 8, 9 or 10% w/w.

In specific embodiments the carbohydrate is raffinose. In one embodiment, the FVIII composition comprises raffinose in a concentration of 2 to 10% w/w, preferably 3 to 8% w/w, preferably 4 to 6% w/w and most preferably 5% w/w. In yet another embodiment the concentration of raffinose is 2, 3, 4, 5, 6, 7, 8, 9 or 10% w/w.

Amino Acids

In one embodiment the composition of the invention further comprises one or more amino acids other than histidine. As used herein, "amino acids" refers to any natural or non-natural pharmaceutically acceptable amino acid. Non-limiting examples of amino acids include, isoleucine, alanine, leucine, asparagine, lysine, aspartic acid, methionine, cysteine, phenylalanine, glutamic acid, threonine, glutamine, tryptophan, glycine, valine, proline, selenocysteine, serine, tyrosine, arginine, histidine, ornithine, taurine, and the like. The amino acid other than histidine is preferably selected from the group consisting of arginine, asparagine, aspartic acid, glutamic acid, glutamine, lysine, methionine, phenylalanine, isoleucine, leucine and combinations thereof.

In one embodiment the aqueous composition comprises arginine and isoleucine.

In one embodiment the aqueous composition comprises arginine, glutamic acid and phenylalanine.

In one embodiment the aqueous composition comprises arginine, glutamic acid, phenylalanine and methionine.

In one embodiment the aqueous composition comprises arginine, isoleucine and methionine.

In one embodiment the aqueous composition comprises glutamine, glutamic acid, isoleucine and methionine.

In one embodiment the concentration of the amino acid other than histidine is at least 0.2 mM, preferably 1 to 300 mM, preferably 5 to 300 mM, preferably 10 to 200 mM, preferably 55 to 150 mM, preferably 25 to 100 mM, preferably 40 to 180 mM, preferably 50 to 90 mM. In yet another embodiment the concentration of the amino acid other than histidine is 0.2, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 mM.

In one embodiment the concentration of the arginine is at least 1 mM, preferably 5 to 300 mM, preferably 10 to 200 mM, preferably 55 to 150 mM, preferably 25 to 100 mM, preferably 40 to 180 mM, preferably 50 to 90 mM. In yet another embodiment the concentration of the arginine is 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 mM.

In one embodiment the concentration of the isoleucine is at least 1 mM, preferably 5 to 300 mM, preferably 10 to 200 mM, preferably 55 to 150 mM, preferably 25 to 100 mM, preferably 40 to 180 mM, preferably 50 to 90 mM. In yet another embodiment the concentration of the isoleucine is 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 mM.

In one embodiment the concentration of the glutamic acid is at least 1 mM, preferably 5 to 300 mM, preferably 10 to 200 mM, preferably 55 to 150 mM, preferably 25 to 100 mM, preferably 40 to 180 mM, preferably 50 to 90 mM. In yet another embodiment the concentration of the glutamic acid is 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 mM.

In one embodiment the concentration of the phenylalanine is at least 1 mM, preferably 5 to 200 mM, preferably 10 to 160 mM, preferably 55 to 150 mM, preferably 25 to 100 mM, preferably 40 to 180 mM, preferably 50 to 90 mM. In yet another embodiment the concentration of the phenylalanine is 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 mM.

Antioxidants

The composition of the present invention may further contain one or more antioxidants(s). An "antioxidant" within the meaning of the present invention is a pharmaceutically compatible compound or composition that decelerates, inhibits, interrupts and/or stops oxidation processes. Antioxidants include, in particular, the following substances: tocopherols and the esters thereof, reduced glutathione, methionine, monothioglycerol, cysteine, homocysteine, cystathionine, vitamin A, sesamol of sesame oil, coniferyl benzoate of benzoin resin, nordihydroguaietic resin and nordihydroguaiaretic acid (NDGA), gallates (among others, methyl, ethyl, propyl, amyl, butyl, lauryl gallates), butylated hydroxyanisole (BHAIBHT, also butyl-p-cresol); ascorbic acid and salts and esters thereof (for example acorbyl palmitate), erythorbinic acid (isoascorbinic acid) and salts and esters thereof, monothioglycerol, sodium formaldehyde sulfoxylate, sodium metabisulfite, sodium bisulfite, sodium sulfite, potassium metabisulfite, butylated hydroxyanisole, butylated hydroxytoluene (BHT), propionic acid. Typical antioxidants are tocopherol such as, for example, a-tocopherol and the esters thereof, butylated hydroxytoluene and butylated hydroxyanisole. The terms "tocopherol" also includes esters of tocopherol. A known tocopherol is a-tocopherol. The term "a-tocopherol" includes esters of a-tocopherol (for example, a-tocopherol acetate). In one embodiment of the invention the antioxidant is methionine, e.g., L-methionine.

In one embodiment, the concentration of the antioxidant is at least 0.05 mM, preferably 0.05 to 100 mM, preferably 0.1 to 80 mM, preferably 0.2 to 50 mM, preferably 0.5 to 70 mM, preferably 1 to 25 mM, preferably 0.1 to 20 mM, preferably 0.25 to 1 mM. In yet another embodiment the concentration of the antioxidant is 0.05, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 6.0, 7.0, 8.0, 9.0, 10.0, 11.0, 12.0, 13.0, 14.0, 15.0, 16.0, 17.0, 18.0, 19.0, 20.0, 25.0, 30.0, 35.0, 40.0, 45.0, 50.0, 55.0, 60.0, 65.0, 70.0, 75.0, 80.0, 85.0, 90.0, 95.0 or 100.0 mM.

In one embodiment, the concentration of methionine is at least 0.05 mM, preferably 0.05 to 100 mM, preferably 0.1 to 80 mM, preferably 0.2 to 50 mM, preferably 0.5 to 70 mM, preferably 1 to 25 mM, preferably 0.1 to 20 mM, preferably 0.25 to 5 mM. In yet another embodiment the concentration of methionine is 0.05, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 6.0, 7.0, 8.0, 9.0, 10.0, 11.0, 12.0, 13.0, 14.0, 15.0, 16.0, 17.0, 18.0, 19.0, 20.0, 25.0, 30.0, 35.0, 40.0, 45.0, 50.0, 55.0, 60.0, 65.0, 70.0, 75.0, 80.0, 85.0, 90.0, 95.0 or 100.0 mM.

In one embodiment, the concentration of glutathione is at least 0.05 mM, preferably 0.05 to 100 mM, preferably 0.1 to 80 mM, preferably 0.2 to 50 mM, preferably 0.5 to 70 mM, preferably 1 to 25 mM, preferably 0.1 to 20 mM, preferably 0.25 to 1 mM. In yet another embodiment the concentration of glutathione is 0.05, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 6.0, 7.0, 8.0, 9.0, 10.0, 11.0, 12.0, 13.0, 14.0, 15.0, 16.0, 17.0, 18.0, 19.0, 20.0, 25.0, 30.0, 35.0, 40.0, 45.0, 50.0, 55.0, 60.0, 65.0, 70.0, 75.0, 80.0, 85.0, 90.0, 95.0 or 100.0 mM.

Stabilizing Agents

The composition of the present invention may comprise a stabilizing agent. As used herein, a "stabilizing agent" refers to a chemical (other synonyms are e.g. "co-solvent", "co-solute", "chemical additive; "excipient") which aids in the stabilization of a labile therapeutic agent in an aqueous formulation either in solution state or during freeze-thawing as well as freeze-drying and subsequent storage of the dehydrated lyophilisate. Examples of suitable stabilizing agents for the formulations and methods provided herein include, without limitation, buffering agents (e.g., TRIS, HEPES, amino acids, etc.), osmolytes (e.g., sugars, sugar alcohols, etc.), cryoprotectants/lyoprotectants (e.g. alcohols such as glycerol, methanol, isopropanol; sugars such as sucrose, xylitol, dextrose, trehalose; carboxylic acids and carboxylates such as lactic acid and lactates, malic acid and maleates; PEGs such as ethylene glycol, PEG 200, PEG 2 000, PEG 20 000; Polymers such as polyvinylpyrrolidons, PVP 12, PVP 17,PVP 30; bulking agents (e.g., amino acids, polyols such as mannitol etc.), salts, polymers, surfactants, antioxidants and the like.

The concentration of the stabilizing agent depends on the chemical nature of the agent and can be chosen in accordance with the disclosure hereinabove.

Stability

In a specific embodiment of the compositions provided above, the composition is stable. The term "stable" as used herein means that the potency of the composition, as measured by a FVIII activity assay, after storage for a period of time, is at least 80% of the potency prior to storage. Unless indicated otherwise herein, the stability testing is carried out as described in the document CPMP/ICH/2736/99 from the European Medicines Agency titled "NOTE FOR GUIDANCE ON STABILITY TESTING: STABILITY TESTING OF NEW DRUG SUBSTANCES AND PRODUCTS" as of August 2003.

In a series of embodiments, the composition provided herein upon lyophilization will be stable for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or more months (25° C.; 40% relative humidity [RH]). In a preferred embodiment, the lyophilized composition will be stable for at least 6 months (25° C.; 40% RH). In a more preferred embodiment, the lyophilized composition will be stable for at least 12 months (25° C.; 40% RH). In another preferred embodiment, the lyophilized composition will be stable for at least 18 months (25° C.; 40% RH). In another preferred embodiment, the lyophilized composition will be stable for at least 24 months (25° C.; 40% RH). In another preferred embodiment, the lyophilized composition will be stable for at least 36 months (25° C.; 40% RH).

In a specific embodiment of the compositions provided above, the lyophilized composition is stable for at least 6 months, preferably for at least 12 months, more preferably for at least 24 months, even more preferably for at least 36 months when stored at 25° C./40% RH.

In another embodiment of the compositions provided above, the lyophilized composition is stable for at least 6 months, preferably for at least 12 months, more preferably for at least 24 months, even more preferably for at least 36 months when stored at 30° C./40% RH.

In another embodiment of the compositions provided above, the lyophilized composition is stable for at least 6 months, preferably for at least 12 months, more preferably for at least 24 months when stored at 40° C./40% RH.

In another embodiment of the compositions provided above, the lyophilized composition is stable for at least 6 months, preferably for at least 12 months, more preferably for at least 24 months, even more preferably for at least 36 months when stored at 25° C./60% RH.

In another embodiment of the compositions provided above, the lyophilized composition is stable for at least 6 months, preferably for at least 12 months, more preferably for at least 24 months, even more preferably for at least 36 months when stored at 30° C./60% RH.

In another embodiment of the compositions provided above, the lyophilized composition is stable for at least 6 months, preferably for at least 12 months, more preferably for at least 24 months when stored at 40° C./60% RH.

In another embodiment of the compositions provided above, the lyophilized composition is stable for at least 6 months, preferably for at least 12 months, more preferably for at least 24 months, even more preferably for at least 36 months when stored at 25° C./65% RH.

In another embodiment of the compositions provided above, the lyophilized composition is stable for at least 6 months, preferably for at least 12 months, more preferably for at least 24 months, even more preferably for at least 36 months when stored at 30° C./65% RH.

In another embodiment of the compositions provided above, the lyophilized composition is stable for at least 6 months, preferably for at least 12 months, more preferably for at least 24 months when stored at 40° C./65% RH.

In another embodiment of the compositions provided above, the lyophilized composition is stable for at least 6 months, preferably for at least 12 months, more preferably for at least 24 months, even more preferably for at least 36 months when stored at 25° C./75% RH.

In another embodiment of the compositions provided above, the lyophilized composition is stable for at least 6 months, preferably for at least 12 months, more preferably for at least 24 months, even more preferably for at least 36 months when stored at 30° C./75% RH.

In another embodiment of the compositions provided above, the lyophilized composition is stable for at least 6 months, preferably for at least 12 months, more preferably for at least 24 months when stored at 40° C./75% RH.

In another embodiment of the compositions provided above, the lyophilized composition is stable for at least 6 months, preferably for at least 12 months, more preferably for at least 24 months, even more preferably for at least 36 months when stored at 25° C./25% RH.

In another embodiment of the compositions provided above, the lyophilized composition is stable for at least 6 months, preferably for at least 12 months, more preferably for at least 24 months, even more preferably for at least 36 months when stored at 30° C./25% RH.

In another embodiment of the compositions provided above, the lyophilized composition is stable for at least 6 months, preferably for at least 12 months, more preferably for at least 24 months when stored at 40° C./25% RH.

Preferably, the amount of high molecular weight components, as determined by SE-HPLC, after storage of the lyophilized composition under one of the conditions defined supra is 3% or less. The amount of high molecular weight components, as determined by SE-HPLC as described in the examples of this application.

In one embodiment the composition is stable for at least 48 hours, preferably for at least 72 hours, more preferably for at least 96 hours, most preferably for at least one week, when stored in the liquid state at 4° C. The aqueous composition typically retains at least 80% of its Factor VIII activity for at least 48 hours, preferably for at least 72 hours, more preferably for at least 96 hours, most preferably for at least one week, when stored in the liquid state at 2 to 8° C. This applies to the aqueous composition prior to lyophilization and/or to the aqueous composition after lyophilization and reconstitution in an aqueous solution, e.g. in distilled water.

In a specific embodiment of the compositions provided above, the composition retains at least 85% of its Factor VIII activity for at least 48 hours, preferably for at least 72 hours, more preferably for at least 96 hours, most preferably for at least one week, when stored in the liquid state at 4° C. This applies to the aqueous composition prior to lyophilization and/or to the aqueous composition after lyophilization and reconstitution in an aqueous solution, e.g. in distilled water.

In a specific embodiment of the compositions provided above, the composition retains at least 90% of its Factor VIII activity for at least 48 hours, preferably for at least 72 hours, more preferably for at least 96 hours, most preferably for at least one week, when stored in the liquid state at 4° C. This applies to the aqueous composition prior to lyophilization and/or to the aqueous composition after lyophilization and reconstitution in an aqueous solution, e.g. in distilled water.

In a specific embodiment of the invention, the composition shows little or no turbidity, e.g. prior to lyophilization or upon lyophilization and reconstitution in water. As used herein, the term "turbidity" refers to the opalescence of a solution. Turbidity can be determined visually or instrumentally, as described in Pharm. Eur. 8.0, section 2.2.1."Clarity and degree of opalescence of liquids". Any reference to turbidity in the present application refers to the methods described in Pharm. Eur. 8.0, section 2.2.1."Clarity and degree of opalescence of liquids".

In one embodiment, the composition of the present invention has a turbidity of 18 NTU or less. In another embodiment, the composition of the present invention has a turbidity of 6 NTU or less. In yet another embodiment, the composition of the present invention has a turbidity of 3 NTU or less. These turbidity values are fulfilled prior to lyophilization and after lyophilization and reconstitution in distilled water.

In yet another embodiment, the composition of the present invention is clear. In the present application, a composition or solution is deemed to be "clear" when its opalescence is not more pronounced than that of "reference suspension III" described in Pharm. Eur. 8.0, section 2.2.1."Clarity and degree of opalescence of liquids". When referring herein to a composition having "no turbidity" or being "free of turbidity", it is to be understood that the composition is "clear" in accordance with this definition.

Preferred are the following compositions (table 1) comprising:

|  | FVIII [IU/ml] | NaCl [mM] | Histidine [mM] | CaCl$_2$ [mM] | Tween ® 80 [% w/w] | Sucrose [% w/w] |
|---|---|---|---|---|---|---|
| composition 1 | 100 | 52 | 100 | 10 | 0.004 | 5 |
| composition 2 | 100 | 40 | 100 | 10 | 0.005 | 5 |
| composition 3 | 100 | 50 | 100 | 10 | 0.005 | 5 |
| composition 4 | 100 | 60 | 100 | 10 | 0.005 | 5 |
| composition 5 | 100 | 70 | 100 | 10 | 0.005 | 5 |
| composition 6 | 100 | 80 | 100 | 10 | 0.005 | 5 |
| composition 7 | 100 | 95 | 100 | 10 | 0.005 | 5 |
| composition 8 | 100 | 50 | 100 | 7 | 0.005 | 5 |
| composition 9 | 100 | 50 | 100 | 10 | 0.005 | 5 |
| composition 10 | 100 | 50 | 100 | 15 | 0.005 | 5 |
| composition 11 | 100 | 50 | 100 | 20 | 0.005 | 5 |
| composition 12 | 100 | 65 | 100 | 10 | 0.005 | 5 |
| composition 13 | 100 | 65 | 100 | 5.5 | 0.005 | 5 |
| composition 14 | 100 | 65 | 55 | 10 | 0.005 | 5 |
| composition 15 | 100 | 65 | 30 | 10 | 0.005 | 5 |
| composition 16 | 100 | 65 | 10 | 10 | 0.005 | 5 |

Further preferred are the following compositions (table 2) comprising:

|  | FVIII [IU/ml] | NaCl [mM] | Histidine [mM] | CaCl$_2$ [mM] | Tween ® 80 [% w/w] | Sucrose [% w/w] |
|---|---|---|---|---|---|---|
| composition 17 | 200 | 52 | 100 | 10 | 0.004 | 5 |
| composition 18 | 200 | 40 | 100 | 10 | 0.005 | 5 |
| composition 19 | 200 | 50 | 100 | 10 | 0.005 | 5 |
| Composition 20 | 200 | 60 | 100 | 10 | 0.005 | 5 |
| composition 21 | 200 | 70 | 100 | 10 | 0.005 | 5 |
| composition 22 | 200 | 80 | 100 | 10 | 0.005 | 5 |
| composition 23 | 200 | 95 | 100 | 10 | 0.005 | 5 |
| composition 24 | 200 | 50 | 100 | 7 | 0.005 | 5 |
| composition 25 | 200 | 50 | 100 | 10 | 0.005 | 5 |
| composition 27 | 200 | 50 | 100 | 15 | 0.005 | 5 |
| composition 28 | 200 | 50 | 100 | 20 | 0.005 | 5 |
| composition 29 | 200 | 65 | 100 | 10 | 0.005 | 5 |
| composition 30 | 200 | 65 | 100 | 5.5 | 0.005 | 5 |
| composition 31 | 200 | 65 | 55 | 10 | 0.005 | 5 |
| composition 32 | 200 | 65 | 30 | 10 | 0.005 | 5 |
| composition 33 | 200 | 65 | 10 | 10 | 0.005 | 5 |

Further preferred are the following compositions (table 3) comprising:

|  | FVIII [IU/ml] | NaCl [mM] | Histidine [mM] | CaCl$_2$ [mM] | Tween ®80 [% w/w] | Sucrose [% w/w] |
|---|---|---|---|---|---|---|
| composition 34 | 400 | 52 | 100 | 10 | 0.004 | 5 |
| composition 35 | 400 | 40 | 100 | 10 | 0.005 | 5 |
| composition 36 | 400 | 50 | 100 | 10 | 0.005 | 5 |
| composition 37 | 400 | 60 | 100 | 10 | 0.005 | 5 |
| composition 38 | 400 | 70 | 100 | 10 | 0.005 | 5 |
| composition 39 | 400 | 80 | 100 | 10 | 0.005 | 5 |
| composition 40 | 400 | 95 | 100 | 10 | 0.005 | 5 |
| composition 41 | 400 | 50 | 100 | 7 | 0.005 | 5 |
| composition 42 | 400 | 50 | 100 | 10 | 0.005 | 5 |

|  | FVIII [IU/ml] | NaCl [mM] | Histidine [mM] | CaCl$_2$ [mM] | Tween ®80 [% w/w] | Sucrose [% w/w] |
| --- | --- | --- | --- | --- | --- | --- |
| composition 43 | 400 | 50 | 100 | 15 | 0.005 | 5 |
| composition 44 | 400 | 50 | 100 | 20 | 0.005 | 5 |
| composition 45 | 400 | 65 | 100 | 10 | 0.005 | 5 |
| composition 46 | 400 | 65 | 100 | 5.5 | 0.005 | 5 |
| composition 47 | 400 | 65 | 55 | 10 | 0.005 | 5 |
| composition 48 | 400 | 65 | 30 | 10 | 0.005 | 5 |
| composition 49 | 400 | 65 | 10 | 10 | 0.005 | 5 |

Further preferred are the following compositions (table 4) comprising:

|  | FVIII [IU/ml] | NaCl [mM] | Histidine [mM] | CaCl$_2$ [mM] | Tween ® 80 [% w/w] | Sucrose [% w/w] |
| --- | --- | --- | --- | --- | --- | --- |
| composition 50 | 800 | 52 | 100 | 10 | 0.004 | 5 |
| composition 51 | 800 | 40 | 100 | 10 | 0.005 | 5 |
| composition 52 | 800 | 50 | 100 | 10 | 0.005 | 5 |
| composition 53 | 800 | 60 | 100 | 10 | 0.005 | 5 |
| composition 54 | 800 | 70 | 100 | 10 | 0.005 | 5 |
| composition 55 | 800 | 80 | 100 | 10 | 0.005 | 5 |
| composition 56 | 800 | 95 | 100 | 10 | 0.005 | 5 |
| composition 57 | 800 | 50 | 100 | 7 | 0.005 | 5 |
| composition 58 | 800 | 50 | 100 | 10 | 0.005 | 5 |
| composition 59 | 800 | 50 | 100 | 15 | 0.005 | 5 |
| composition 60 | 800 | 50 | 100 | 20 | 0.005 | 5 |
| composition 61 | 800 | 65 | 100 | 10 | 0.005 | 5 |
| composition 62 | 800 | 65 | 100 | 5.5 | 0.005 | 5 |
| composition 63 | 800 | 65 | 55 | 10 | 0.005 | 5 |
| composition 64 | 800 | 65 | 30 | 10 | 0.005 | 5 |
| composition 65 | 800 | 65 | 10 | 10 | 0.005 | 5 |

Further preferred are the following compositions (table 5) comprising:

|  | FVIII [IU/ml] | NaCl [mM] | Histidine [mM] | CaCl$_2$ [mM] | Tween ®80 [% w/w] | Sucrose [% w/w] |
| --- | --- | --- | --- | --- | --- | --- |
| composition 66 | 1200 | 52 | 100 | 10 | 0.004 | 5 |
| composition 67 | 1200 | 40 | 100 | 10 | 0.005 | 5 |
| composition 68 | 1200 | 50 | 100 | 10 | 0.005 | 5 |
| composition 69 | 1200 | 60 | 100 | 10 | 0.005 | 5 |
| composition 70 | 1200 | 70 | 100 | 10 | 0.005 | 5 |
| composition 71 | 1200 | 80 | 100 | 10 | 0.005 | 5 |
| composition 72 | 1200 | 95 | 100 | 10 | 0.005 | 5 |
| composition 73 | 1200 | 50 | 100 | 7 | 0.005 | 5 |
| composition 74 | 1200 | 50 | 100 | 10 | 0.005 | 5 |
| composition 75 | 1200 | 50 | 100 | 15 | 0.005 | 5 |
| composition 76 | 1200 | 50 | 100 | 20 | 0.005 | 5 |
| composition 77 | 1200 | 65 | 100 | 10 | 0.005 | 5 |
| composition 78 | 1200 | 65 | 100 | 5.5 | 0.005 | 5 |
| composition 79 | 1200 | 65 | 55 | 10 | 0.005 | 5 |
| composition 80 | 1200 | 65 | 30 | 10 | 0.005 | 5 |
| composition 81 | 1200 | 65 | 10 | 10 | 0.005 | 5 |

Preferred are the following compositions (table 6) comprising:

|  | FVIII [IU/ml] | NaCl [mM] | Histidine [mM] | CaCl$_2$ [mM] | Tween ® 80 [% w/w] | Sucrose [% w/w] |
| --- | --- | --- | --- | --- | --- | --- |
| composition 82 | 1500 | 52 | 100 | 10 | 0.004 | 5 |
| composition 83 | 1500 | 40 | 100 | 10 | 0.005 | 5 |
| composition 84 | 1500 | 50 | 100 | 10 | 0.005 | 5 |
| composition 85 | 1500 | 60 | 100 | 10 | 0.005 | 5 |
| composition 86 | 1500 | 70 | 100 | 10 | 0.005 | 5 |
| composition 87 | 1500 | 80 | 100 | 10 | 0.005 | 5 |

-continued

|  | FVIII [IU/ml] | NaCl [mM] | Histidine [mM] | CaCl$_2$ [mM] | Tween ® 80 [% w/w] | Sucrose [% w/w] |
| --- | --- | --- | --- | --- | --- | --- |
| composition 88 | 1500 | 95 | 100 | 10 | 0.005 | 5 |
| composition 89 | 1500 | 50 | 100 | 7 | 0.005 | 5 |
| composition 90 | 1500 | 50 | 100 | 10 | 0.005 | 5 |
| composition 91 | 1500 | 50 | 100 | 15 | 0.005 | 5 |
| composition 92 | 1500 | 50 | 100 | 20 | 0.005 | 5 |
| composition 93 | 1500 | 65 | 100 | 10 | 0.005 | 5 |
| composition 94 | 1500 | 65 | 100 | 5.5 | 0.005 | 5 |
| composition 95 | 1500 | 65 | 55 | 10 | 0.005 | 5 |
| composition 96 | 1500 | 65 | 30 | 10 | 0.005 | 5 |
| composition 97 | 1500 | 65 | 10 | 10 | 0.005 | 5 |

Preferred are the following compositions (table 7) comprising:

|  | FVIII [IU/ml] | NaCl [mM] | Histidine [mM] | CaCl$_2$ [mM] | Tween ®80 [% w/w] | Sucrose [% w/w] |
| --- | --- | --- | --- | --- | --- | --- |
| composition 98 | 2500 | 52 | 100 | 10 | 0.004 | 5 |
| composition 99 | 2500 | 40 | 100 | 10 | 0.005 | 5 |
| composition 100 | 2500 | 50 | 100 | 10 | 0.005 | 5 |
| composition 101 | 2500 | 60 | 100 | 10 | 0.005 | 5 |
| composition 102 | 2500 | 70 | 100 | 10 | 0.005 | 5 |
| composition 103 | 2500 | 80 | 100 | 10 | 0.005 | 5 |
| composition 104 | 2500 | 95 | 100 | 10 | 0.005 | 5 |
| composition 105 | 2500 | 50 | 100 | 7 | 0.005 | 5 |
| composition 106 | 2500 | 50 | 100 | 10 | 0.005 | 5 |
| composition 107 | 2500 | 50 | 100 | 15 | 0.005 | 5 |
| composition 108 | 2500 | 50 | 100 | 20 | 0.005 | 5 |
| composition 109 | 2500 | 65 | 100 | 10 | 0.005 | 5 |
| composition 110 | 2500 | 65 | 100 | 5.5 | 0.005 | 5 |
| composition 111 | 2500 | 65 | 55 | 10 | 0.005 | 5 |
| composition 112 | 2500 | 65 | 30 | 10 | 0.005 | 5 |
| composition 113 | 2500 | 65 | 10 | 10 | 0.005 | 5 |

Preferred are the following compositions (table 8) comprising:

|  | FVIII [IU/ml] | NaCl [mM] | Histidine [mM] | CaCl$_2$ [mM] | Tween ® 80 [% w/w] | Sucrose [% w/w] | Arginine [mM] | Isoleucine [mM] | Glutamate [mM] | Phenyl-alanin [mM] | Methionine [mM] | Glutathione [mM] |
| --- | --- | --- | --- | --- | --- | --- | --- | --- | --- | --- | --- | --- |
| composition 114 | 100 | 80 | 100 | 10 | 0.005 | 5 | 25 | 25 | — | — | — | — |
| Composition 115 | 100 | 80 | 100 | 10 | 0.005 | 5 | 25 | 25 | — | — | 50 | — |
| composition 116 | 100 | 80 | 100 | 10 | 0.005 | 5 | 25 | — | 25 | 25 | — | — |
| composition 117 | 100 | 80 | 100 | 10 | 0.005 | 5 | 25 | — | 25 | 25 | 50 | — |
| composition 118 | 100 | 80 | 100 | 10 | 0.005 | 5 | 25 | 25 | — | — | — | 5 |
| composition 119 | 100 | 80 | 100 | 10 | 0.005 | 5 | 25 | — | 25 | 25 | 50 | 5 |
| composition 120 | 100 | 80 | 100 | 10 | 0.005 | 5 | 100 | — | 100 | 50 | 50 | — |
| composition 121 | 100 | 80 | 100 | 10 | 0.005 | 5 | 100 | — | 100 | 50 | 50 | 5 |

Preferred are the following compositions (table 9) comprising:

|  | FVIII [IU/ml] | NaCl [mM] | Histidine [mM] | CaCl$_2$ [mM] | Tween ®80 [% w/w] | Sucrose [% w/w] | Arginine [mM] | Isoleucine [mM] | Glutamate [mM] | Phenyl-alanin [mM] | Methionine [mM] | Glutathione [mM] |
| --- | --- | --- | --- | --- | --- | --- | --- | --- | --- | --- | --- | --- |
| composition 122 | 200 | 80 | 100 | 10 | 0.005 | 5 | 25 | 25 | — | — | — | — |
| composition 123 | 200 | 80 | 100 | 10 | 0.005 | 5 | 25 | 25 | — | — | 50 | — |
| composition 124 | 200 | 80 | 100 | 10 | 0.005 | 5 | 25 | — | 25 | 25 | — | — |
| composition 125 | 200 | 80 | 100 | 10 | 0.005 | 5 | 25 | — | 25 | 25 | 50 | — |
| composition 126 | 200 | 80 | 100 | 10 | 0.005 | 5 | 25 | 25 | — | — | — | 5 |
| composition 127 | 200 | 80 | 100 | 10 | 0.005 | 5 | 25 | — | 25 | 25 | 50 | 5 |
| composition 128 | 200 | 80 | 100 | 10 | 0.005 | 5 | 100 | — | 100 | 50 | 50 | — |
| composition 129 | 200 | 80 | 100 | 10 | 0.005 | 5 | 100 | — | 100 | 50 | 50 | 5 |

Preferred are the following compositions (table 10) comprising:

| | FVIII [IU/ml] | NaCl [mM] | Histidine [mM] | CaCl$_2$ [mM] | Tween ®80 [% w/w] | Sucrose [% w/w] | Arginine [mM] | Isoleucine [mM] | Glutamate [mM] | Phenylalanin [mM] | Methionine [mM] | Glutathione [mM] |
|---|---|---|---|---|---|---|---|---|---|---|---|---|
| composition 130 | 400 | 80 | 100 | 10 | 0.005 | 5 | 25 | 25 | — | — | — | — |
| composition 131 | 400 | 80 | 100 | 10 | 0.005 | 5 | 25 | 25 | — | — | 50 | — |
| composition 132 | 400 | 80 | 100 | 10 | 0.005 | 5 | 25 | — | 25 | 25 | — | — |
| composition 133 | 400 | 80 | 100 | 10 | 0.005 | 5 | 25 | — | 25 | 25 | 50 | — |
| composition 134 | 400 | 80 | 100 | 10 | 0.005 | 5 | 25 | 25 | — | — | — | 5 |
| composition 135 | 400 | 80 | 100 | 10 | 0.005 | 5 | 25 | — | 25 | 25 | 50 | 5 |
| composition 136 | 400 | 80 | 100 | 10 | 0.005 | 5 | 100 | — | 100 | 50 | 50 | — |
| composition 137 | 400 | 80 | 100 | 10 | 0.005 | 5 | 100 | — | 100 | 50 | 50 | 5 |

Preferred are the following compositions (table 11) comprising:

| | FVIII [IU/ml] | NaCl [mM] | Histidine [mM] | CaCl$_2$ [mM] | Tween ®80 [% w/w] | Sucrose [% w/w] | Arginine [mM] | Isoleucine [mM] | Glutamate [mM] | Phenylalanin [mM] | Methionine [mM] | Glutathione [mM] |
|---|---|---|---|---|---|---|---|---|---|---|---|---|
| composition 138 | 800 | 80 | 100 | 10 | 0.005 | 5 | 25 | 25 | — | — | — | — |
| composition 139 | 800 | 80 | 100 | 10 | 0.005 | 5 | 25 | 25 | — | — | 50 | — |
| composition 140 | 800 | 80 | 100 | 10 | 0.005 | 5 | 25 | — | 25 | 25 | — | — |
| composition 141 | 800 | 80 | 100 | 10 | 0.005 | 5 | 25 | — | 25 | 25 | 50 | — |
| composition 142 | 800 | 80 | 100 | 10 | 0.005 | 5 | 25 | 25 | — | — | — | 5 |
| composition 143 | 800 | 80 | 100 | 10 | 0.005 | 5 | 25 | — | 25 | 25 | 50 | 5 |
| composition 144 | 800 | 80 | 100 | 10 | 0.005 | 5 | 100 | — | 100 | 50 | 50 | — |
| composition 145 | 800 | 80 | 100 | 10 | 0.005 | 5 | 100 | — | 100 | 50 | 50 | 5 |

Preferred are the following compositions (table 12) comprising:

| | FVIII [IU/ml] | NaCl [mM] | Histidine [mM] | CaCl$_2$ [mM] | Tween ®80 [% w/w] | Sucrose [% w/w] | Arginine [mM] | Isoleucine [mM] | Glutamate [mM] | Phenylalanin [mM] | Methionine [mM] | Glutathione [mM] |
|---|---|---|---|---|---|---|---|---|---|---|---|---|
| composition 146 | 1200 | 80 | 100 | 10 | 0.005 | 5 | 25 | 25 | — | — | — | — |
| composition 147 | 1200 | 80 | 100 | 10 | 0.005 | 5 | 25 | 25 | — | — | 50 | — |
| composition 148 | 1200 | 80 | 100 | 10 | 0.005 | 5 | 25 | — | 25 | 25 | — | — |
| composition 149 | 1200 | 80 | 100 | 10 | 0.005 | 5 | 25 | — | 25 | 25 | 50 | — |
| composition 150 | 1200 | 80 | 100 | 10 | 0.005 | 5 | 25 | 25 | — | — | — | 5 |
| composition 151 | 1200 | 80 | 100 | 10 | 0.005 | 5 | 25 | — | 25 | 25 | 50 | 5 |
| composition 152 | 1200 | 80 | 100 | 10 | 0.005 | 5 | 100 | — | 100 | 50 | 50 | — |
| composition 153 | 1200 | 80 | 100 | 10 | 0.005 | 5 | 100 | — | 100 | 50 | 50 | 5 |

Preferred are the following compositions (table 13) comprising:

| | FVIII [IU/ml] | NaCl [mM] | Histidine [mM] | CaCl$_2$ [mM] | Tween ®80 [% w/w] | Sucrose [% w/w] | Arginine [mM] | Isoleucine [mM] | Glutamate [mM] | Phenylalanin [mM] | Methionine [mM] | Glutathione [mM] |
|---|---|---|---|---|---|---|---|---|---|---|---|---|
| composition 154 | 1500 | 80 | 100 | 10 | 0.005 | 5 | 25 | 25 | — | — | — | — |
| composition 155 | 1500 | 80 | 100 | 10 | 0.005 | 5 | 25 | 25 | — | — | 50 | — |
| composition 156 | 1500 | 80 | 100 | 10 | 0.005 | 5 | 25 | — | 25 | 25 | — | — |
| composition 157 | 1500 | 80 | 100 | 10 | 0.005 | 5 | 25 | — | 25 | 25 | 50 | — |
| composition 158 | 1500 | 80 | 100 | 10 | 0.005 | 5 | 25 | 25 | — | — | — | 5 |
| composition 159 | 1500 | 80 | 100 | 10 | 0.005 | 5 | 25 | — | 25 | 25 | 50 | 5 |
| composition 160 | 1500 | 80 | 100 | 10 | 0.005 | 5 | 100 | — | 100 | 50 | 50 | — |
| composition 161 | 1500 | 80 | 100 | 10 | 0.005 | 5 | 100 | — | 100 | 50 | 50 | 5 |

Preferred are the following compositions (table 14) comprising:

| | FVIII [IU/ml] | NaCl [mM] | Histidine [mM] | CaCl$_2$ [mM] | Tween ®80 [% w/w] | Sucrose [% w/w] | Arginine [mM] | Isoleucine [mM] | Glutamate [mM] | Phenylalanin [mM] | Methionine [mM] | Glutathione [mM] |
|---|---|---|---|---|---|---|---|---|---|---|---|---|
| composition 162 | 2500 | 80 | 100 | 10 | 0.005 | 5 | 25 | 25 | — | — | — | — |
| composition 163 | 2500 | 80 | 100 | 10 | 0.005 | 5 | 25 | 25 | — | — | 50 | — |
| composition 164 | 2500 | 80 | 100 | 10 | 0.005 | 5 | 25 | — | 25 | 25 | — | — |
| composition 165 | 2500 | 80 | 100 | 10 | 0.005 | 5 | 25 | — | 25 | 25 | 50 | — |
| composition 166 | 2500 | 80 | 100 | 10 | 0.005 | 5 | 25 | 25 | — | — | — | 5 |
| composition 167 | 2500 | 80 | 100 | 10 | 0.005 | 5 | 25 | — | 25 | 25 | 50 | 5 |
| composition 168 | 2500 | 80 | 100 | 10 | 0.005 | 5 | 100 | — | 100 | 50 | 50 | — |
| composition 169 | 2500 | 80 | 100 | 10 | 0.005 | 5 | 100 | — | 100 | 50 | 50 | 5 |

Preferred are the following compositions (table 15) comprising:

| | NaCl [mM] | Histidine [mM] | CaCl$_2$ [mM] | Sucrose [% w/w] |
|---|---|---|---|---|
| composition 170 | 40-195 | at least 20 | at least 8 | 2-10 |
| composition 171 | 40-195 | at least 20 | at least 8 | 3-8 |
| composition 172 | 40-195 | at least 20 | at least 8 | 4-6 |
| composition 173 | 40-195 | at least 20 | at least 8 | 5 |
| composition 174 | 40-195 | at least 20 | at least 10 | 2-10 |
| composition 175 | 40-195 | at least 20 | at least 10 | 3-8 |
| composition 176 | 40-195 | at least 20 | at least 10 | 4-6 |
| composition 177 | 40-195 | at least 20 | at least 10 | 5 |
| composition 178 | 40-195 | at least 20 | 8-20 | 2-10 |
| composition 179 | 40-195 | at least 20 | 8-20 | 3-8 |
| composition 180 | 40-195 | at least 20 | 8-20 | 4-6 |
| composition 181 | 40-195 | at least 20 | 8-20 | 5 |
| composition 182 | 40-195 | at least 20 | 8-50 | 2-10 |
| composition 183 | 40-195 | at least 20 | 8-50 | 3-8 |
| composition 184 | 40-195 | at least 20 | 8-50 | 4-6 |
| composition 185 | 40-195 | at least 20 | 8-50 | 5 |
| composition 186 | 40-195 | at least 50 | at least 6.5 | 2-10 |
| composition 187 | 40-195 | at least 50 | at least 6.5 | 3-8 |
| composition 188 | 40-195 | at least 50 | at least 6.5 | 4-6 |
| composition 189 | 40-195 | at least 50 | at least 6.5 | 5 |
| composition 190 | 40-195 | at least 50 | at least 10 | 2-10 |
| composition 191 | 40-195 | at least 50 | at least 10 | 3-8 |
| composition 192 | 40-195 | at least 50 | at least 10 | 4-6 |
| composition 193 | 40-195 | at least 50 | at least 10 | 5 |
| composition 194 | 40-195 | at least 50 | 6.5-20 | 2-10 |
| composition 195 | 40-195 | at least 50 | 6.5-20 | 3-8 |
| composition 196 | 40-195 | at least 50 | 6.5-20 | 4-6 |
| composition 197 | 40-195 | at least 50 | 6.5-20 | 5 |
| composition 198 | 40-195 | at least 50 | 6.5-50 | 2-10 |
| composition 199 | 40-195 | at least 50 | 6.5-50 | 3-8 |
| composition 200 | 40-195 | at least 50 | 6.5-50 | 4-6 |
| composition 201 | 40-195 | at least 50 | 6.5-50 | 5 |
| composition 202 | 40-195 | 50-100 | at least 6.5 | 2-10 |
| composition 203 | 40-195 | 50-100 | at least 6.5 | 3-8 |
| composition 204 | 40-195 | 50-100 | at least 6.5 | 4-6 |
| composition 205 | 40-195 | 50-100 | at least 6.5 | 5 |
| composition 206 | 40-195 | 50-100 | at least 10 | 2-10 |
| composition 207 | 40-195 | 50-100 | at least 10 | 3-8 |
| composition 208 | 40-195 | 50-100 | at least 10 | 4-6 |
| composition 209 | 40-195 | 50-100 | at least 10 | 5 |
| composition 210 | 40-195 | 50-100 | 6.5-20 | 2-10 |
| composition 211 | 40-195 | 50-100 | 6.5-20 | 3-8 |
| composition 212 | 40-195 | 50-100 | 6.5-20 | 4-6 |
| composition 213 | 40-195 | 50-100 | 6.5-20 | 5 |
| composition 214 | 40-195 | 50-100 | 6.5-50 | 2-10 |
| composition 215 | 40-195 | 50-100 | 6.5-50 | 3-8 |
| composition 216 | 40-195 | 50-100 | 6.5-50 | 4-6 |
| composition 217 | 40-195 | 50-100 | 6.5-50 | 5 |
| composition 218 | 40-195 | 100 | at least 4 | 2-10 |
| composition 219 | 40-195 | 100 | at least 4 | 3-8 |
| composition 220 | 40-195 | 100 | at least 4 | 4-6 |
| composition 221 | 40-195 | 100 | at least 4 | 5 |
| composition 222 | 40-195 | 100 | at least 10 | 2-10 |
| composition 223 | 40-195 | 100 | at least 10 | 3-8 |
| composition 224 | 40-195 | 100 | at least 10 | 4-6 |
| composition 225 | 40-195 | 100 | at least 10 | 5 |
| composition 226 | 40-195 | 100 | 4-20 | 2-10 |
| composition 227 | 40-195 | 100 | 4-20 | 3-8 |
| composition 228 | 40-195 | 100 | 4-20 | 4-6 |
| composition 229 | 40-195 | 100 | 4-20 | 5 |
| composition 230 | 40-195 | 100 | 4-50 | 2-10 |
| composition 231 | 40-195 | 100 | 4-50 | 3-8 |
| composition 232 | 40-195 | 100 | 4-50 | 4-6 |
| composition 233 | 40-195 | 100 | 4-50 | 5 |

In another embodiment the compositions 170-233 further comprise a surfactant, e.g. Polyoxyethylene (20) sorbitan monooleate [e.g. Tween® 80], preferably at a concentration of at least 0.001% w/w.

In another embodiment the compositions 170-233 further comprise one or more amino acids other than histidine. The other amino acid is selected from the list consisting of arginine, asparagine, aspartic acid, glutamic acid, glutamine, lysine, methionine, phenylalanine, isoleucine or mixtures thereof, preferably at a concentration of at least 1 mM.

In another embodiment the compositions 170-233 further comprise an antioxidant, preferably at a concentration at least 0.05 mM. Examples of antioxidants include, but are not limited to reduced glutathione, methionine, cysteine, sodium sulfite, vitamin A, vitamin E, ascorbic acid, sodium ascorbate and mixtures thereof. In one embodiment of the invention the antioxidant is methionine, e.g., L-methionine.

In another embodiment, the compositions 170-233 have a pH of 6.0-8.0 or 6.5-7.5 or 6.8-7.2 or 7.

In another embodiment the compositions 170-233 further comprise
 a. Polyoxyethylene (20) sorbitan monooleate [e.g. Tween® 80] as a surfactant, preferably at a concentration of at least 0.001% w/w,
 b. one or more amino acids other than histidine selected from the list consisting of arginine, asparagine, aspartic acid, glutamic acid, glutamine, lysine, methionine, phenylalanine, isoleucine or mixtures thereof, preferably at a concentration of at least 1 mM,
 c. an antioxidant selected from the list consisting of reduced glutathione, methionine, cysteine, sodium sulfite, vitamin A, vitamin E, ascorbic acid, sodium ascorbate and mixtures thereof, preferably at a concentration of at least 0.05 mM and
 d. the compositions have a pH of 6.0-8.0 or 6.5-7.5 or 6.8-7.2 or 7.

Preferred are the following compositions (table 16) comprising:

| | NaCl [mM] | Histidine [mM] | CaCl₂ [mM] | Sucrose [% w/w] |
|---|---|---|---|---|
| composition 234 | 50-95 | at least 20 | at least 8 | 2-10 |
| composition 235 | 50-95 | at least 20 | at least 8 | 3-8 |
| composition 236 | 50-95 | at least 20 | at least 8 | 4-6 |
| composition 237 | 50-95 | at least 20 | at least 8 | 5 |
| composition 238 | 50-95 | at least 20 | at least 10 | 2-10 |
| composition 239 | 50-95 | at least 20 | at least 10 | 3-8 |
| composition 240 | 50-95 | at least 20 | at least 10 | 4-6 |
| composition 241 | 50-95 | at least 20 | at least 10 | 5 |
| composition 242 | 50-95 | at least 20 | 8-20 | 2-10 |
| composition 243 | 50-95 | at least 20 | 8-20 | 3-8 |
| composition 244 | 50-95 | at least 20 | 8-20 | 4-6 |
| composition 245 | 50-95 | at least 20 | 8-20 | 5 |
| composition 246 | 50-95 | at least 20 | 8-50 | 2-10 |
| composition 247 | 50-95 | at least 20 | 8-50 | 3-8 |
| composition 248 | 50-95 | at least 20 | 8-50 | 4-6 |
| composition 249 | 50-95 | at least 20 | 8-50 | 5 |
| composition 250 | 50-95 | at least 50 | at least 6.5 | 2-10 |
| composition 251 | 50-95 | at least 50 | at least 6.5 | 3-8 |
| composition 252 | 50-95 | at least 50 | at least 6.5 | 4-6 |
| composition 253 | 50-95 | at least 50 | at least 6.5 | 5 |
| composition 254 | 50-95 | at least 50 | at least 10 | 2-10 |
| composition 255 | 50-95 | at least 50 | at least 10 | 3-8 |
| composition 256 | 50-95 | at least 50 | at least 10 | 4-6 |
| composition 257 | 50-95 | at least 50 | at least 10 | 5 |
| compositon 258 | 50-95 | at least 50 | 6.5-20 | 2-10 |
| compositon 259 | 50-95 | at least 50 | 6.5-20 | 3-8 |
| compositon 260 | 50-95 | at least 50 | 6.5-20 | 4-6 |
| compositon 261 | 50-95 | at least 50 | 6.5-20 | 5 |
| compositon 262 | 50-95 | at least 50 | 6.5-50 | 2-10 |
| compositon 263 | 50-95 | at least 50 | 6.5-50 | 3-8 |
| compositon 264 | 50-95 | at least 50 | 6.5-50 | 4-6 |
| compositon 265 | 50-95 | at least 50 | 6.5-50 | 5 |
| compositon 266 | 50-95 | 50-100 | at least 6.5 | 2-10 |
| compositon 267 | 50-95 | 50-100 | at least 6.5 | 3-8 |
| compositon 268 | 50-95 | 50-100 | at least 6.5 | 4-6 |
| compositon 269 | 50-95 | 50-100 | at least 6.5 | 5 |
| compositon 270 | 50-95 | 50-100 | at least 10 | 2-10 |
| compositon 271 | 50-95 | 50-100 | at least 10 | 3-8 |
| compositon 272 | 50-95 | 50 100 | at least 10 | 4-6 |
| compositon 273 | 50-95 | 50-100 | at least 10 | 5 |
| compositon 274 | 50-95 | 50-100 | 6.5-20 | 2-10 |
| compositon 275 | 50-95 | 50-100 | 6.5-20 | 3-8 |
| compositon 276 | 50-95 | 50-100 | 6.5-20 | 4-6 |
| compositon 277 | 50-95 | 50-100 | 6.5-20 | 5 |
| compositon 278 | 50-95 | 50-100 | 6.5-50 | 2-10 |
| compositon 279 | 50-95 | 50-100 | 6.5-50 | 3-8 |
| compositon 280 | 50-95 | 50-100 | 6.5-50 | 4-6 |
| compositon 281 | 50-95 | 50-100 | 6.5-50 | 5 |
| compositon 282 | 50-95 | 100 | at least 4 | 2-10 |
| compositon 283 | 50-95 | 100 | at least 4 | 3-8 |
| compositon 284 | 50-95 | 100 | at least 4 | 4-6 |
| compositon 285 | 50-95 | 100 | at least 4 | 5 |
| compositon 286 | 50-95 | 100 | at least 10 | 2-10 |
| compositon 287 | 50-95 | 100 | at least 10 | 3-8 |
| compositon 288 | 50-95 | 100 | at least 10 | 4-6 |
| compositon 289 | 50-95 | 100 | at least 10 | 5 |
| compositon 290 | 50-95 | 100 | 4-20 | 2-10 |
| compositon 291 | 50-95 | 100 | 4-20 | 3-8 |
| compositon 292 | 50-95 | 100 | 4-20 | 4-6 |
| compositon 293 | 50-95 | 100 | 4-20 | 5 |
| compositon 294 | 50-95 | 100 | 4-50 | 2-10 |
| compositon 295 | 50-95 | 100 | 4-50 | 3-8 |
| compositon 296 | 50-95 | 100 | 4-50 | 4-6 |
| compositon 297 | 50-95 | 100 | 4-50 | 5 |

In another embodiment the compositions 234-297 further comprise a surfactant, e.g. Polyoxyethylene (20) sorbitan monooleate [e.g. Tween® 80], preferably at a concentration of at least 0.001 w/w.

In another embodiment the compositions 234-297 further comprise one or more amino acids other than histidine. The other amino acid is selected from the list consisting of arginine, asparagine, aspartic acid, glutamic acid, glutamine, lysine, methionine, phenylalanine, isoleucine or mixtures thereof, preferably at a concentration of at least 1 mM.

In another embodiment the compositions 234-297 further comprise an antioxidant, preferably at a concentration at least 0.05 mM. Examples of antioxidants include, but are not limited to reduced glutathione, methionine, cysteine, sodium sulfite, vitamin A, vitamin E, ascorbic acid, sodium ascorbate and mixtures thereof. In one embodiment of the invention the antioxidant is methionine, e.g., L-methionine.

In another embodiment, the compositions 234-297 have a pH of 6.0-8.0 or 6.5-7.5 or 6.8-7.2 or 7.

In another embodiment the compositions 234-297 further comprise
  e. Polyoxyethylene (20) sorbitan monooleate [e.g. Tween® 80] as a surfactant, preferably at a concentration of at least 0.001% w/w,
  f. one or more amino acids other than histidine selected from the list consisting of arginine, asparagine, aspartic acid, glutamic acid, glutamine, lysine, methionine, phenylalanine, isoleucine or mixtures thereof, preferably at a concentration of at least 1 mM,
  g. an antioxidant selected from the list consisting of reduced glutathione, methionine, cysteine, sodium sulfite, vitamin A, vitamin E, ascorbic acid, sodium ascorbate and mixtures thereof, preferably at a concentration of at least 0.05 mM and
  h. the compositions have a pH of 6.0-8.0 or 6.5-7.5 or 6.8-7.2 or 7.

Preferred are the following compositions (table 17) comprising:

| | NaCl [mM] | Histidine [mM] | CaCl₂ [mM] | Sucrose [% w/w] |
|---|---|---|---|---|
| compositon 298 | 60-75, e.g. 65 | at least 20 | at least 8 | 2-10 |
| compositon 299 | 60-75, e.g. 65 | at least 20 | at least 8 | 3-8 |
| compositon 300 | 60-75, e.g. 65 | at least 20 | at least 8 | 4-6 |
| compositon 301 | 60-75, e.g. 65 | at least 20 | at least 8 | 5 |
| compositon 302 | 60-75, e.g. 65 | at least 20 | at least 10 | 2-10 |
| compositon 303 | 60-75, e.g. 65 | at least 20 | at least 10 | 3-8 |
| compositon 304 | 60-75, e.g. 65 | at least 20 | at least 10 | 4-6 |
| compositon 305 | 60-75, e.g. 65 | at least 20 | at least 10 | 5 |
| compositon 306 | 60-75, e.g. 65 | at least 20 | 8-20 | 2-10 |
| compositon 307 | 60-75, e.g. 65 | at least 20 | 8-20 | 3-8 |
| compositon 308 | 60-75, e.g. 65 | at least 20 | 8-20 | 4-6 |
| compositon 309 | 60-75, e.g. 65 | at least 20 | 8-20 | 5 |
| compositon 310 | 60-75, e.g. 65 | at least 20 | 8-50 | 2-10 |
| compositon 311 | 60-75, e.g. 65 | at least 20 | 8-50 | 3-8 |
| compositon 312 | 60-75, e.g. 65 | at least 20 | 8-50 | 4-6 |
| compositon 313 | 60-75, e.g. 65 | at least 20 | 8-50 | 5 |
| compositon 314 | 60-75, e.g. 65 | at least 50 | at least 6.5 | 2-10 |
| compositon 315 | 60-75, e.g. 65 | at least 50 | at least 6.5 | 3-8 |
| compositon 316 | 60-75, e.g. 65 | at least 50 | at least 6.5 | 4-6 |
| compositon 317 | 60-75, e.g. 65 | at least 50 | at least 6.5 | 5 |
| compositon 318 | 60-75, e.g. 65 | at least 50 | at least 10 | 2-10 |
| compositon 319 | 60-75, e.g. 65 | at least 50 | at least 10 | 3-8 |
| compositon 320 | 60-75, e.g. 65 | at least 50 | at least 10 | 4-6 |
| compositon 321 | 60-75, e.g. 65 | at least 50 | at least 10 | 5 |
| compositon 322 | 60-75, e.g. 65 | at least 50 | 6.5-20 | 2-10 |
| compositon 323 | 60-75, e.g. 65 | at least 50 | 6.5-20 | 3-8 |
| compositon 324 | 60-75, e.g. 65 | at least 50 | 6.5-20 | 4-6 |
| compositon 325 | 60-75, e.g. 65 | at least 50 | 6.5-20 | 5 |
| compositon 326 | 60-75, e.g. 65 | at least 50 | 6.5-50 | 2-10 |
| compositon 327 | 60-75, e.g. 65 | at least 50 | 6.5-50 | 3-8 |
| compositon 328 | 60-75, e.g. 65 | at least 50 | 6.5-50 | 4-6 |
| compositon 329 | 60-75, e.g. 65 | at least 50 | 6.5-50 | 5 |
| compositon 330 | 60-75, e.g. 65 | 50-100 | at least 6.5 | 2-10 |
| compositon 331 | 60-75, e.g. 65 | 50-100 | at least 6.5 | 3-8 |
| compositon 332 | 60-75, e.g. 65 | 50-100 | at least 6.5 | 4-6 |
| compositon 333 | 60-75, e.g. 65 | 50-100 | at least 6.5 | 5 |
| compositon 334 | 60-75, e.g. 65 | 50-100 | at least 10 | 2-10 |
| compositon 335 | 60-75, e.g. 65 | 50-100 | at least 10 | 3-8 |
| compositon 336 | 60-75, e.g. 65 | 50-100 | at least 10 | 4-6 |
| compositon 337 | 60-75, e.g. 65 | 50-100 | at least 10 | 5 |
| compositon 338 | 60-75, e.g. 65 | 50-100 | 6.5-20 | 2-10 |
| compositon 339 | 60-75, e.g. 65 | 50-100 | 6.5-20 | 3-8 |

-continued

| | NaCl [mM] | Histidine [mM] | CaCl$_2$ [mM] | Sucrose [% w/w] |
|---|---|---|---|---|
| compositon 340 | 60-75, e.g. 65 | 50-100 | 6.5-20 | 4-6 |
| compositon 341 | 60-75, e.g. 65 | 50-100 | 6.5-20 | 5 |
| compositon 342 | 60-75, e.g. 65 | 50-100 | 6.5-50 | 2-10 |
| compositon 343 | 60-75, e.g. 65 | 50-100 | 6.5-50 | 3-8 |
| compositon 344 | 60-75, e.g. 65 | 50-100 | 6.5-50 | 4-6 |
| compositon 345 | 60-75, e.g. 65 | 50-100 | 6.5-50 | 5 |
| compositon 346 | 60-75, e.g. 65 | 100 | at least 6.5 | 2-10 |
| compositon 347 | 60-75, e.g. 65 | 100 | at least 6.5 | 3-8 |
| compositon 348 | 60-75, e.g. 65 | 100 | at least 6.5 | 4-6 |
| compositon 349 | 60-75, e.g. 65 | 100 | at least 6.5 | 5 |
| compositon 350 | 60-75, e.g. 65 | 100 | at least 10 | 2-10 |
| compositon 351 | 60-75, e.g. 65 | 100 | at least 10 | 3-8 |
| compositon 352 | 60-75, e.g. 65 | 100 | at least 10 | 4-6 |
| compositon 353 | 60-75, e.g. 65 | 100 | at least 10 | 5 |
| compositon 354 | 60-75, e.g. 65 | 100 | 6.5-20 | 2-10 |
| compositon 355 | 60-75, e.g. 65 | 100 | 6.5-20 | 3-8 |
| compositon 356 | 60-75, e.g. 65 | 100 | 6.5-20 | 4-6 |
| compositon 357 | 60-75, e.g. 65 | 100 | 6.5-20 | 5 |
| compositon 358 | 60-75, e.g. 65 | 100 | 6.5-50 | 2-10 |
| compositon 359 | 60-75, e.g. 65 | 100 | 6.5-50 | 3-8 |
| compositon 360 | 60-75, e.g. 65 | 100 | 6.5-50 | 4-6 |
| compositon 361 | 60-75, e.g. 65 | 100 | 6.5-50 | 5 |

In another embodiment the compositions 298-361 further comprise a surfactant, e.g. Polyoxyethylene (20) sorbitan monooleate [e.g. Tween® 80], preferably at a concentration of at least 0.001% w/w.

In another embodiment the compositions 298-361 further comprise one or more amino acids other than histidine. The other amino acid is selected from the list consisting of arginine, asparagine, aspartic acid, glutamic acid, glutamine, lysine, methionine, phenylalanine, isoleucine or mixtures thereof, preferably at a concentration of at least 1 mM.

In another embodiment the compositions 298-361 further comprise an antioxidant, preferably at a concentration at least 0.05 mM. Examples of antioxidants include, but are not limited to reduced glutathione, methionine, cysteine, sodium sulfite, vitamin A, vitamin E, ascorbic acid, sodium ascorbate and mixtures thereof. In one embodiment of the invention the antioxidant is methionine, e.g., L-methionine.

In another embodiment, the compositions 298-361 have a pH of 6.0-8.0 or 6.5-7.5 or 6.8-7.2 or 7.

In another embodiment the compositions 298-361 further comprise
i. Polyoxyethylene (20) sorbitan monooleate [e.g. Tween® 80] as a surfactant, preferably at a concentration of at least 0.001% w/w,
j. one or more amino acids other than histidine selected from the list consisting of arginine, asparagine, aspartic acid, glutamic acid, glutamine, lysine, methionine, phenylalanine, isoleucine or mixtures thereof, preferably at a concentration of at least 1 mM,
k. an antioxidant selected from the list consisting of reduced glutathione, methionine, cysteine, sodium sulfite, vitamin A, vitamin E, ascorbic acid, sodium ascorbate and mixtures thereof, preferably at a concentration of at least 0.05 mM and
l. the compositions have a pH of 6.0-8.0 or 6.5-7.5 or 6.8-7.2 or 7.

In a specific embodiment the invention relates to a composition obtainable by lyophilizing the aqueous composition described above. In another embodiment, the invention relates to a composition obtained by lyophilizing the aqueous composition described above.

In a specific embodiment the invention relates to a composition obtainable by reconstituting the lyophilized aqueous composition as described above with a suitable solvent.

In a specific embodiment a composition is obtainable by reconstituting the lyophilized aqueous composition as described above with a suitable solvent, wherein the suitable solvent is an aqueous solution.

In a specific embodiment a composition is obtainable by reconstituting the lyophilized aqueous composition as described above with an aqueous solution, wherein the aqueous solution is selected from the group comprising Ringer's solution, Ringer's lactate solution, and any other suitable solution for parenteral application.

In a specific embodiment a composition is obtainable by reconstituting the lyophilized aqueous composition as described above with an aqueous solution, wherein the aqueous solution is water, preferably "water for injection".

In a specific embodiment a composition is obtainable by reconstituting the lyophilized aqueous composition as described above with an aqueous solution, wherein the aqueous solution is a sodium chloride solution.

In a specific embodiment a composition is obtainable by reconstituting the lyophilized aqueous composition as described above with an aqueous solution, wherein the aqueous solution is a histidine solution.

Another aspect of the invention is the use of a composition described herein in the treatment of a blood coagulation disorder, e.g. hemophilia A.

In a specific embodiment of the compositions provided above, the composition is formulated for subcutaneous and/or intramuscular administration.

The compositions are administered orally, topically, transdermally, parenterally, by inhalation spray, vaginally, rectally or by intracranial injection, preferably parenterally. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and/or surgical implantation at a particular site is contemplated as well. Generally, compositions are essentially free of pyrogens (see e.g. Ph. Eur. 7.0/2.06.08.00), as well as other impurities that could be harmful to the recipient.

EXAMPLES

The following examples were carried out using a FVIII molecule (SEQ ID NO:2; construct dBN(64-53) described in WO 2004/067566). This FVIII molecule will be referred to as "CSL627" in the following.

Chromogenic FVIII:C Assay

The chromogenic FVIII:C assay was performed using the Coamatic FVIII test kit (Chromogenix-Instrumentation Laboratory SpA V. le Monza 338-20128 Milano, Italy).

Principle of the assay: In the presence of calcium and phospholipid, Factor X is activated by Factor IXa to Factor Xa. This reaction is stimulated by Factor VIIIa as cofactor. F VIIIa is formed by low amounts of thrombin in the reaction mixture from F VIII in the sample to be measured. When using the optimum concentrations of $Ca^{2+}$, phospholipid and Factor IXa and an excess quantity of Factor X, activation of Factor X is proportional to the potency of Factor VIII. Activated Factor X releases the chromophore pNA from the chromogenic substrate S-2765. The release of pNA, measured at 405 nm, is therefore proportional to the amount of FXa formed and, therefore, also to the Factor VIII activity of the sample. The assay was adapted to be performed on automated coagulation analyzers, either the Behring Coagulation Timer (BCT) or Behring Coagulation System (BCS), both from Siemens Healthcare Diagnostics GmbH, Ludwig-Erhard-Straße 12, 65760 Eschborn, Germany.

One Stage Coagulation Assay

The FVIII:C one stage coagulation assay was performed using the Pathromtin SL reagent and FVIII deficient plasma, both from Siemens Healthcare Diagnostics products GmbH, Emil-von-Behring-Str. 76, 35041 Marburg, Germany.

Principle of the assay: The test is executed as a modified version of the activated Partial Thromboplastin Time (aPTT)-assay: Incubation of plasma with phospholipids and a surface activator leads to the activation of factors of the intrinsic coagulation system. Addition of calcium ions triggers the coagulation cascade. The time to formation of a measurable fibrin clot is measured. The assay is executed in the presence of Factor VIII deficient plasma. The coagulation capability of the deficient plasma is restored by Coagulation Factor VIII included in the sample to be tested. The shortening of coagulation time is proportional to the amount of Factor VIII present in the sample. The activity of Coagulation Factor VIII is quantified by direct comparison to a standard preparation with a known activity of Factor VIII in International Units.

The assay was adapted to be performed on automated coagulation analyzers, either the Behring Coagulation Timer (BCT) or Behring Coagulation System (BCS), both from Siemens Healthcare Diagnostics GmbH, Ludwig-Erhard-Straße 12, 65760 Eschborn, Germany.

High Molecular Weight Components (HMWC) by Size Exclusion HPLC

The size exclusion HPLC was performed using a COSMOSIL Diol-300-II 7.5×600 mm column (Nacalai Tesque, Kyoto, Japan) and fluorescence detection at excitation wavelength 280 nm and emission wavelength 340 nm. The composition of the mobile phase was 300 mM NaCl, 20 mM HEPES, 10 mM $CaCl_2*2H_2O$, 0.005% Tween® 80, 10% Isopropanol, pH 7.0. Elution was isocratic at a flow rate of 0.5 mL/min at ambient room temperature over 75 minutes.

Example 1

Preparation of FVIII Formulations and Evaluation of the Solution Properties Following Buffer Exchange via Desalting Columns Purified CSL627 at a FVIII:C activity (chromogenic substrate method) of 9500 IU/ml was formulated into the desired compositions by buffer exchange via NAP-25 desalting columns (GE Healthcare Sephadex™ G 25; Cat. No. 17-0852-01) according to the suppliers instructions. This buffer exchange resulted in a dilution factor of 1.4.

The different compositions were then investigated for their appearance (turbidity) and yield in FVIII:C activity.

The yield of FVIII:C was calculated as the percentage of the amount of FVIII:C in the obtained composition following buffer exchange divided by the amount of FVIII:C in the solution prior to buffer exchange with appropriate adjustment for dilution by the buffer exchange (dilution factor 1.4).

TABLE 18

| Formulation no # | NaCl [mM] | Sucrose [% w/v] | Histidine [mM] | CaCl$_2$ [mM] | Tween ® 80 [% v/v] | turbid yes/no | FVIII:C Yield * [%] |
|---|---|---|---|---|---|---|---|
| 01-001 | 80 | 5 | 100 | 10 | 0.005 | no | 112 |
| 01-002 (comparative) | 10 | 5 | 100 | 10 | 0.005 | yes | 48 |
| 01-003 (comparative) | 30 | 5 | 100 | 10 | 0.005 | yes | 98 |

* FVIII:C activity yield determined via a chromogenic substrate activity assay following buffer exchange via desalting columns Example 2

Preparation of FVIII Formulations and Evaluation of the Solution Properties Following Buffer Exchange Via Desalting Columns The different compositions were obtained by buffer exchange as described in example 1 (FVIII:C activity in the starting material was 9733 IU/mL). The compositions were evaluated for their appearance following buffer exchange. In addition the compositions were then sterile filtered (0.22 µm) and assayed for their FVIII:C activity directly upon filtration (time 0) and following storage at +2-+8° C. for 1, 2, 3, 15, 30, and 60 days and storage at +25° C. and +40° C. for 1, 2 and 3 days.

The recovery (stability) was calculated as the percentage of FVIII:C (Chromogenic substrate FVIII activity assay) after storage divided by the FVIII:C activity at Time 0. The FVIII:C activity at Time 0 (after 0.22 µm filtration) was defined as 100%.

TABLE 19

| | | | | | | | | Stability: FVIII:C Coamatic Recovery * [%] | | | | | |
|---|---|---|---|---|---|---|---|---|---|---|---|---|---|
| | | | | | | | | +2 to +8° C. | | | | | |
| Form. no # | NaCl [mM] | Sucrose [% w/v] | Histidine [mM] | CaCl$_2$ [mM] | Tween ® 80 [% v/v] | turbid yes/no | Time 0 | 1 day | 2 days | 3 days | 15 days | 30 days | 60 days |
| 02-001 | 40 | 5 | 100 | 10 | 0.005 | no | 100 | 103 | 107 | 100 | 97 | 97 | 93 |
| 02-002 | 50 | 5 | 100 | 10 | 0.005 | no | 100 | 96 | 104 | 97 | 92 | 90 | 81 |
| 02-003 | 60 | 5 | 100 | 10 | 0.005 | no | 100 | 102 | 111 | 114 | 105 | 98 | 85 |
| 02-004 | 70 | 5 | 100 | 10 | 0.005 | no | 100 | 110 | 98 | 104 | 93 | 94 | 87 |
| 02-005 | 80 | 5 | 100 | 10 | 0.005 | no | 100 | 100 | 106 | 102 | 100 | 93 | 91 |

TABLE 19-continued

| | | | | | | | Stability: FVIII:C Coamatic Recovery * [%] +2 to +8° C. | | | | | | |
|---|---|---|---|---|---|---|---|---|---|---|---|---|---|
| Form. no # | NaCl [mM] | Sucrose [% w/v] | Histidine [mM] | CaCl$_2$ [mM] | Tween ® 80 [% v/v] | turbid yes/no | Time 0 | 1 day | 2 days | 3 days | 15 days | 30 days | 60 days |
| 02-006 | 100 | 5 | 100 | 10 | 0.005 | no | 100 | 100 | 111 | 106 | 101 | 96 | 87 |
| 02-007 | 150 | 5 | 100 | 10 | 0.005 | no | 100 | 98 | 109 | 110 | 92 | 88 | 85 |

* FVIII:C recovery based on FVIII:C activity measurements (Chromogenic substrate activity assay) following storage at different temperature conditions (stability test in liquid state)

TABLE 20

| | | | | | | | Stability: FVIII:C Coamatic Recovery * [%] +25° C. | | |
|---|---|---|---|---|---|---|---|---|---|
| Form. no # | NaCl [mM] | Sucrose [% w/v] | Histidine [mM] | CaCl$_2$ [mM] | Tween ® 80 [% v/v] | turbid yes/no | Time 0 | 1 day | 2 days | 3 days |
| 02-001 | 40 | 5 | 100 | 10 | 0.005 | no | 100 | 104 | 105 | 103 |
| 02-002 | 50 | 5 | 100 | 10 | 0.005 | no | 100 | 95 | 95 | 102 |
| 02-003 | 60 | 5 | 100 | 10 | 0.005 | no | 100 | 105 | 104 | 116 |
| 02-004 | 70 | 5 | 100 | 10 | 0.005 | no | 100 | 104 | 96 | 100 |
| 02-005 | 80 | 5 | 100 | 10 | 0.005 | no | 100 | 99 | 103 | 96 |
| 02-006 | 100 | 5 | 100 | 10 | 0.005 | no | 100 | 107 | 102 | 105 |
| 02-007 | 150 | 5 | 100 | 10 | 0.005 | no | 100 | 106 | 103 | 103 |

* FVIII:C recovery based on FVIII:C activity measurements (Chromogenic substrate activity assay) following storage at different temperature conditions (stability test in liquid state)

TABLE 21

| | | | | | | | Stability: FVIII:C Coamatic Recovery * [%] +40° C. | | |
|---|---|---|---|---|---|---|---|---|---|
| Form. no # | NaCl [mM] | Sucrose [% w/v] | Histidine [mM] | CaCl$_2$ [mM] | Tween ® 80 [% v/v] | turbid yes/no | Time 0 | 1 day | 2 days | 3 days |
| 02-001 | 40 | 5 | 100 | 10 | 0.005 | no | 100 | 103 | 93 | 101 |
| 02-002 | 50 | 5 | 100 | 10 | 0.005 | no | 100 | 91 | 89 | 93 |
| 02-003 | 60 | 5 | 100 | 10 | 0.005 | no | 100 | 102 | 105 | 104 |
| 02-004 | 70 | 5 | 100 | 10 | 0.005 | no | 100 | 96 | 97 | 97 |
| 02-005 | 80 | 5 | 100 | 10 | 0.005 | no | 100 | 107 | 91 | 89 |
| 02-006 | 100 | 5 | 100 | 10 | 0.005 | no | 100 | 105 | 95 | 93 |
| 02-007 | 150 | 5 | 100 | 10 | 0.005 | no | 100 | 105 | 104 | 103 |

* FVIII:C recovery based on FVIII:C activity measurements (Chromogenic substrate activity assay) following storage at different temperature conditions (stability test in liquid state)

Example 3

Appearance of the Solution Following Buffer Exchange Via Desalting Columns

The different compositions were obtained by buffer exchange as described in example 1 (FVIII:C activity by chromogenic substrate FVIII activity assay in the starting material was 8317 IU/mL). The compositions were evaluated for their appearance following buffer exchange.

TABLE 22

| Form. no # | NaCl [mM] | Sucrose [% w/v] | Histidine [mM] | CaCl$_2$ [mM] | Tween ® 80 [% v/v] | turbid yes/no |
|---|---|---|---|---|---|---|
| 03-001 (comparative) | 0 | 5 | 100 | 10 | 0.005 | yes |
| 03-002 (comparative) | 10 | 5 | 100 | 10 | 0.005 | yes |
| 03-003 (comparative) | 20 | 5 | 100 | 10 | 0.005 | yes |
| 03-004 (comparative) | 30 | 5 | 100 | 10 | 0.005 | yes |
| 03-005 | 40 | 5 | 100 | 10 | 0.005 | no |

TABLE 22-continued

| Form. no # | NaCl [mM] | Sucrose [% w/v] | Histidine [mM] | CaCl$_2$ [mM] | Tween ® 80 [% v/v] | turbid yes/no |
|---|---|---|---|---|---|---|
| 03-006 | 50 | 5 | 100 | 10 | 0.005 | no |
| 03-007 | 80 | 5 | 100 | 10 | 0.005 | no |
| 03-008 | 80 | 0.5 | 100 | 10 | 0.005 | no |
| 03-009 | 80 | 5 | 20 | 10 | 0.005 | no |
| 03-010 (comparative) | 80 | 5 | 100 | 3 | 0.005 | yes |
| 03-011 (comparative) | 80 | 0.5 | 20 | 3 | 0.005 | yes |
| 03-012 | 80 | 0.5 | 20 | 10 | 0.005 | no |
| 03-013 (comparative) | 80 | 0.5 | 100 | 3 | 0.005 | yes |
| 03-014 (comparative) | 80 | 5 | 20 | 3 | 0.005 | yes |

Example 4

Yield in FVIII:C activity and appearance of the solution following buffer exchange via desalting columns and recovery of FVIII:C activity upon storage.

The different compositions were obtained by buffer exchange as described in example 1 (FVIII:C activity in the starting material was 4780 IU/mL).

The compositions were evaluated for their appearance following buffer exchange. In addition the compositions were then sterile filtered (0.22 μm) and assayed for their FVIII:C activity (Chromogenic substrate assay) directly upon filtration (time 0) and following storage at 2-8° C. for 1, 2 and 3 days and storage at 25° C. and 40° C. for 3 days.

The yield of the formulation process in FVIII:C activity was calculated as the percentage of FVIII:C in the obtained composition following buffer exchange divided by the FVIII:C in the solution prior to buffer exchange with appropriate adjustment for dilutions. The recovery (stability) upon storage was calculated as the percentage of FVIII:C after storage divided by the FVIII:C activity at Time 0. The FVIII:C activity at Time 0 (after 0.22 μm filtration) was defined as 100%.

TABLE 23

| | | | | | | | | | Stability: FVIII:C Coamatic Recovery ** [%] | | | | |
|---|---|---|---|---|---|---|---|---|---|---|---|---|---|
| | | | | | | | | | +2 to +8° C. | | | +25° C. | +40° C. |
| | NaCl | Sucrose | Histidine | CaCl$_2$ | Tween® 80 | turbid | FVIII:C Coamatic | Time | 1 | 2 | 3 | 3 | 3 |
| Form. no # | [mM] | [% w/v] | [mM] | [mM] | [% v/v] | yes/no | Yield * [%] | 0 | days | days | days | days | days |
| 04-001 | 80 | 5 | 100 | 10 | 0.005 | no | 99 | 100 | n/a | n/a | 88 | 88 | 81 |
| 04-002 (comparative) | 50 | 5 | 100 | 1 | 0.005 | yes | 76 | 100 | n/a | n/a | 88 | 72 | 74 |
| 04-003 | 50 | 5 | 100 | 7 | 0.005 | no | 95 | 100 | n/a | n/a | 90 | 95 | 81 |
| 04-004 | 50 | 5 | 100 | 10 | 0.005 | no | 98 | 100 | n/a | n/a | 93 | 93 | 80 |
| 04-005 | 50 | 5 | 100 | 15 | 0.005 | no | 93 | 100 | n/a | n/a | 92 | 94 | 83 |
| 04-006 | 50 | 5 | 100 | 20 | 0.005 | no | 94 | 100 | n/a | n/a | 92 | 96 | 81 |

* FVIII:C yield (based on FVIII activity measurements with a chromogenic substrate FVIII activity assay) following buffer exchange via desalting columns
** FVIII:C recovery (based on FVIII activity measurements with a chromogenic substrate FVIII activity assay) following storage at different temperature conditions (stability test in liquid state)

Example 5

HMWC Formation (SE-HPLC) in Freeze-Dried Preparations Upon Storage at Elevated Temperature.

The FVIII:C activity and the concentration of the excipients of the formulations of this example were adjusted by diluting a FVIII concentrate with appropriate buffer solutions. The formulations obtained showed FVIII:C concentrations of 430-480 IU/mL. The solutions were then dispensed (2.5 mL) and freeze-dried. The obtained lyophilisates were stored at +40° C. and samples taken after 1, 3, 6 and 12 months. Samples were taken from the reconstituted solutions prior to and following storage of the lyophilisates and frozen at −70° C. HMWC were determined by SE-HPLC in the samples following thawing in a water bath (+37° C.).

TABLE 24

| | | | | | | Storage stability of lyophilisates: HMWC by SE-HPLC [%] | | | | |
|---|---|---|---|---|---|---|---|---|---|---|
| | NaCl | Sucrose | Histidine | CaCl$_2$ | Tween ® 80 | after FD | +40° C. | | | |
| Form. no # | [mM] | [% w/v] | [mM] | [mM] | [% v/v] | (Time 0) | 1 month | 3 month | 6 month | 12 month |
| 05-001 | 52 | 5 | 100 | 10 | 0.004 | 0.76 | 1.39 | 0.41 | 0.25 | 0.73 |
| 05-002 (comparative) | 280 | 0.6 | 20 | 3.4 | 0.02 | 0.56 | 2.89 | 3.16 | 6.13 | 5.75 |
| 05-003 (comparative) | 340 | 2.55 | 52.5 | 5.5 | 0.05 | 0.30 | 2.07 | 2.18 | 2.79 | 4.17 |
| 05-004 (comparative) | 340 | 2.55 | 52.5 | 0.64 | 0.05 | 0.34 | 2.24 | 2.15 | 2.97 | 4.48 |
| 05-005 (comparative) | 340 | 2.55 | 3.61 | 5.5 | 0.05 | 0.31 | 1.84 | 2.19 | 3.50 | 5.69 |
| 05-006 (comparative) | 600 | 5 | 3.61 | 0.64 | 0.1 | 0.38 | 3.38 | 3.86 | 7.21 | 11.43 |
| 05-007 (comparative) | 600 | 5 | 3.61 | 10 | 0.004 | 1.44 | 1.81 | 1.81 | 5.48 | 7.73 |
| 05-008 (comparative) | 600 | 5 | 100 | 0.64 | 0.004 | 1.03 | 1.64 | 2.18 | 4.90 | 6.71 |

Example 6

FVIII:C Chromogenic Substrate Activity Assay and HMWC Formation (SE-HPLC) in Freeze-Dried Preparations Upon Storage at Elevated Temperature The FVIII:C activity and the concentration of the excipients were adjusted by diluting a FVIII concentrate with appropriate buffer solutions. The solutions were then dispensed (2.5 mL) and freeze-dried. The obtained lyophilisates were stored at +40° C. and samples taken after 1, 3, 6, 12, 18 and 24 months. Samples were taken from the reconstituted solutions prior to and following storage of the lyophilisates and frozen at −70° C. HMWC were determined in the samples stored frozen following thawing in a water bath (+37° C.).

FVIII:C activity (Chromogenic substrate FVIII activity assay) was determined in the fresh solutions prior to freeze-drying and in the fresh reconstituted lyophilisates directly following freeze-drying or after storage. The recovery (stability) was calculated as the percentage of FVIII:C after storage divided by the FVIII:C activity at Time 0. The FVIII:C activity at Time 0 (After freeze-drying) was defined as 100%.

TABLE 25

| | | | | | | | FVIII:C activity prior to freeze- drying | | Storage stability of lyophilisates: FVIII:C Coamatic Recovery [%] | | | | | | |
|---|---|---|---|---|---|---|---|---|---|---|---|---|---|---|---|
| | | | | | | | | after FD | +40° C. | | | | | | |
| Form. no # | NaCl [mM] | Sucrose [% w/v] | Histi- dine [mM] | CaCl$_2$ [mM] | Tween ® 80 [% v/v] | dosage form [IU] | [IU/ml] | (Time 0) | 1 month | 3 month | 6 month | 9 month | 12 month | 18 month | 24 month |
| 06-001 (com- par- ative) | 280 | 0.6 | 20 | 3.4 | 0.02 | 500 | 219 | 100 | 94 | 84 | 86 | 64 | 58 | 50 | 46 |
| 06-002 | 80 | 5 | 100 | 10 | 0.005 | 500 | 218 | 100 | 96 | 96 | 98 | 91 | 81 | 89 | 100 |
| 06-003 (com- par- ative) | 280 | 0.6 | 20 | 3.4 | 0.02 | 1000 | 437 | 100 | 106 | 87 | 88 | 78 | 65 | 59 | 55 |
| 06-004 | 80 | 5 | 100 | 10 | 0.005 | 1000 | 428 | 100 | 103 | 102 | 110 | 96 | 86 | 87 | 93 |
| 06-005 (com- par- ative) | 280 | 0.6 | 20 | 3.4 | 0.02 | 3000 | 1440 | 100 | 91 | 83 | 74 | 69 | 55 | 57 | 42 |
| 06-006 | 80 | 5 | 100 | 10 | 0.005 | 3000 | 1368 | 100 | 84 | 89 | 94 | 86 | n.a. | 82 | 89 |

TABLE 26

| | | | | | | | FVIII:C activity prior to freeze- drying | after FD | Storage stability of lyophilisates: HMWC by SE-HPLC [%] | | | | | | |
|---|---|---|---|---|---|---|---|---|---|---|---|---|---|---|---|
| | | | | | | | | | +40° C. | | | | | | |
| Form. no # | NaCl [mM] | Sucrose [% w/v] | Histi- dine [mM] | CaCl$_2$ [mM] | Tween ® 80 [% v/v] | dosage form [IU] | [IU/ml] | (Time 0) | 1 month | 3 month | 6 month | 9 month | 12 month | 18 month | 24 month |
| 06-001 (com- par- ative) | 280 | 0.6 | 20 | 3.4 | 0.02 | 500 | 219 | 0.28 | 2.99 | 2.24 | 2.99 | 3.91 | 3.65 | 12.14 | 7.19 |

TABLE 26-continued

| Form. no # | NaCl [mM] | Sucrose [% w/v] | Histi-dine [mM] | CaCl$_2$ [mM] | Tween ® 80 [% v/v] | dosage form [IU] | FVIII:C activity prior to freeze-drying [IU/ml] | after FD (Time 0) | Storage stability of lyophilisates: HMWC by SE-HPLC [%] +40° C. | | | | | | |
|---|---|---|---|---|---|---|---|---|---|---|---|---|---|---|---|
| | | | | | | | | | 1 month | 3 month | 6 month | 9 month | 12 month | 18 month | 24 month |
| 06-002 | 80 | 5 | 100 | 10 | 0.005 | 500 | 218 | 0.13 | 0.13 | 0.30 | 0.56 | 0.66 | 0.74 | 1.42 | 0.79 |
| 06-003 (comparative) | 280 | 0.6 | 20 | 3.4 | 0.02 | 1000 | 437 | 0.59 | 1.94 | 5.00 | 4.26 | 3.29 | 3.91 | 6.88 | 7.13 |
| 06-004 | 80 | 5 | 100 | 10 | 0.005 | 1000 | 428 | 0.23 | 0.50 | 0.96 | 1.25 | 0.58 | 0.73 | 1.46 | 1.72 |
| 06-005 (comparative) | 280 | 0.6 | 20 | 3.4 | 0.02 | 3000 | 1440 | 0.53 | 2.50 | 4.86 | 9.56 | 4.51 | 9.12 | 6.95 | 15.95 |
| 06-006 | 80 | 5 | 100 | 10 | 0.005 | 3000 | 1368 | 0.13 | 0.33 | 0.38 | 0.31 | 1.04 | n.a. | 1.02 | 2.03 |

Example 7

Preparation of FVIII Formulations and Evaluation of the Solution Properties Following Buffer Exchange Via Desalting Columns.

Purified CSL627 was formulated into the desired compositions by buffer exchange via NAP-25 desalting columns (GE Healthcare Sephadex™ G 25; Cat. No. 17-0852-01) according to the suppliers instructions and as described in example 1. Subsequently, the different compositions were diluted based on the chromogenic activity assay to obtain a FVIII:C activity (potency) using a chromogenic substrate FVIII activity assay of about 7000 IU/mL. The different compositions were then investigated for their appearance (turbidity).

Results are shown graphically in FIG. 1. Dots represent a turbidity above a threshold level of 18 NTU, diamonds represent a clear solution (turbidity less than or equal to 18 NTU).

Example 8

HMWC Formation (SE-HPLC) in Freeze-Dried Preparations Upon Storage at Elevated Temperature The FVIII:C activity and the concentration of the excipients of the formulations of this example were adjusted by diluting a FVIII concentrate (CSL627) with appropriate buffer solutions. The formulations obtained showed FVIII:C concentrations of about 390-435 IU/mL. The solutions were then dispensed (2.5 mL) and freeze-dried. The obtained

TABLE 27

| Form. no # | NaCl [mM] | Sucrose [% w/v] | Histidine [mM] | CaCl$_2$ [mM] | GSH [mM] | Tween ® 80 (%) | turbid yes/no |
|---|---|---|---|---|---|---|---|
| 07-001 | 65 | 5.0 | 100 | 10 | 0.25 | 0.005 | no |
| 07-002 | 65 | 5.0 | 100 | 10 | 0.25 | 0.005 | no |
| 07-003 | 65 | 5.0 | 100 | 5.5 | 0.25 | 0.005 | no |
| 07-004 (comparative) | 65 | 5.0 | 100 | 3.0 | 0.25 | 0.005 | yes |
| 07-005 (comparative) | 65 | 5.0 | 100 | 1.0 | 0.25 | 0.005 | yes |
| 07-006 | 65 | 5.0 | 55 | 10 | 0.25 | 0.005 | no |
| 07-007 (comparative) | 65 | 5.0 | 55 | 5.5 | 0.25 | 0.005 | yes |
| 07-008 (comparative) | 65 | 5.0 | 55 | 5.5 | 0.25 | 0.005 | yes |
| 07-009 (comparative) | 65 | 5.0 | 55 | 5.5 | 0.25 | 0.005 | yes |
| 07-010 (comparative) | 65 | 5.0 | 55 | 3.0 | 0.25 | 0.005 | yes |
| 07-011 (comparative) | 65 | 5.0 | 55 | 1.0 | 0.25 | 0.005 | yes |
| 07-012 | 65 | 5.0 | 30 | 10 | 0.25 | 0.005 | no |
| 07-013 (comparative) | 65 | 5.0 | 30 | 5.5 | 0.25 | 0.005 | yes |
| 07-014 (comparative) | 65 | 5.0 | 30 | 1.0 | 0.25 | 0.005 | yes |
| 07-015 | 65 | 5.0 | 10 | 10 | 0.25 | 0.005 | no |
| 07-016 (comparative) | 65 | 5.0 | 10 | 5.5 | 0.25 | 0.005 | yes |
| 07-017 (comparative) | 65 | 5.0 | 10 | 3.0 | 0.25 | 0.005 | yes |
| 07-018 (comparative) | 65 | 5.0 | 10 | 1.0 | 0.25 | 0.005 | yes | lyophilisates were stored at +40° C. and samples taken after 1, 3, 6, 9 and 12 months. Samples were taken from the reconstituted solutions prior to and following storage of the lyophilisates and frozen at −70° C. HMWC were determined by SE-HPLC in the samples following thawing in a water bath (+37° C.).

TABLE 28

Storage stability of lyophilisates: HMWC by SE-HPLC [%]

| | | | | | | | | +40° C. | | | | |
|---|---|---|---|---|---|---|---|---|---|---|---|---|
| Form. no # | NaCl [mM] | Sucrose [% w/v] | Histidine [mM] | CaCl$_2$ [mM] | GSH [mM] | Tween® 80 [% v/v] | after FD (Time 0) | 1 month | 3 month | 6 month | 9 month | 12 month |
| 08-001 (comparative) | 500 | 5.0 | 100 | 10 | 0.25 | 0.005 | 1.27 | 1.27 | 2.22 | 3.11 | 2.92 | 4.77 |
| 08-002 (comparative) | 300 | 5.0 | 100 | 10 | 0.25 | 0.005 | 0.29 | 0.58 | 1.06 | 1.86 | 2.04 | 1.92 |
| 08-003 | 150 | 5.0 | 100 | 10 | 0.25 | 0.005 | 0.47 | 0.42 | 0.68 | 0.74 | 0.81 | 0.56 |
| 08-004 | 100 | 5.0 | 100 | 10 | 0.25 | 0.005 | 0.32 | 0.40 | 0.74 | 0.65 | 0.72 | 0.62 |
| 08-005 | 65 | 5.0 | 100 | 15 | 0.25 | 0.005 | 0.34 | 0.34 | 0.84 | 0.77 | 0.96 | 0.75 |
| 08-006 | 65 | 5.0 | 100 | 10 | 0.25 | 0.005 | 0.34 | 0.42 | 0.77 | 0.67 | 0.87 | 0.72 |
| 08-007 | 65 | 5.0 | 100 | 7 | 0.25 | 0.005 | 0.53 | 0.51 | 0.78 | 0.79 | 1.10 | 0.87 |
| 08-008 | 65 | 5.0 | 100 | 5 | 0.25 | 0.005 | 0.49 | 0.53 | 0.93 | 0.83 | 1.17 | 0.84 |

Example 9

FVIII:C Chromogenic Substrate Activity Assay and HMWC Formation (SE-HPLC) in Freeze-Dried Preparations Upon Storage at Elevated Temperature The FVIII:C activity and the concentration of the excipients were adjusted by diluting a FVIII concentrate (CSL627) with appropriate buffer solutions. The solutions were then dispensed (2.5 mL) and freeze-dried. The obtained lyophilisates were stored at +40° C. and samples taken after 1, 3, 6, 9 and 12 months. Samples were taken from the reconstituted solutions prior to and following storage of the lyophilisates and frozen at −70° C. HMWC were determined in the samples stored frozen following thawing in a water bath (+37° C.).

FVIII:C activity (Chromogenic substrate FVIII activity assay) was determined in the fresh solutions prior to freeze-drying and in the fresh reconstituted lyophilisates directly following freeze-drying or after storage. The recovery (stability) was calculated as the percentage of FVIII:C after storage divided by the FVIII:C activity at Time 0. The FVIII:C activity at Time 0 (After freeze-drying) was defined as 100%.

TABLE 29

| | | | | | | | FVIII:C dosage form [IU] | activity prior to freeze-drying [IU/ml] | Storage stability of lyophilisates: FVIII:C Coamatic Recovery [%] | | | | |
|---|---|---|---|---|---|---|---|---|---|---|---|---|---|
| | | | | | | | | | after FD (Time 0) | +40° C. | | | |
| Form. no # | NaCl [mM] | Sucrose [% w/v] | Histidine [mM] | CaCl$_2$ [mM] | GSH [mM] | Tween® 80 [% v/v] | | | | 1 month | 3 month | 6 month | 9 month | 12 month |
| 09-001 | 65 | 5.0 | 100 | 10 | 0.25 | 0.005 | 1000 | 417 | 100 | 102 | 100 | 96 | 100 | 106 |
| 09-002 | 65 | 5.0 | 100 | 10 | 0.25 | 0.005 | 1000 | 447 | 100 | 107 | 103 | 93 | 93 | 95 |
| 09-003 | 65 | 5.0 | 100 | 5.5 | 0.25 | 0.005 | 1000 | 411 | 100 | 98 | 104 | 90 | 93 | 91 |
| 09-004 | 65 | 5.0 | 55 | 10 | 0.25 | 0.005 | 1000 | 389 | 100 | 103 | 105 | 95 | 105 | 107 |
| 09-005 | 65 | 5.0 | 30 | 10 | 0.25 | 0.005 | 1000 | 383 | 100 | 108 | 100 | 97 | 98 | 102 |
| 09-006 | 65 | 5.0 | 10 | 10 | 0.25 | 0.005 | 1000 | 384 | 100 | 110 | 101 | 95 | 94 | 90 |

TABLE 30

| | | | | | | | FVIII:C dosage form [IU] | activity prior to freeze-drying [IU/ml] | Storage stability of lyophilisates: HMWC by SE-HPLC [%] (n.t. = not tested) | | | | |
|---|---|---|---|---|---|---|---|---|---|---|---|---|---|
| | | | | | | | | | after FD (Time 0) | +40° C. | | | |
| Form. no # | NaCl [mM] | Sucrose [% w/v] | Histidine [mM] | CaCl$_2$ [mM] | GSH [mM] | Tween® 80 [% v/v] | | | | 1 month | 3 month | 6 month | 9 month | 12 month |
| 09-001 | 65 | 5.0 | 100 | 10 | 0.25 | 0.005 | 1000 | 417 | 0.19 | n.t. | 0.64 | 0.39 | 0.87 | n.t. |
| 09-002 | 65 | 5.0 | 100 | 10 | 0.25 | 0.005 | 1000 | 447 | 0.39 | n.t. | 0.57 | 0.46 | 0.64 | n.t. |
| 09-003 | 65 | 5.0 | 100 | 5.5 | 0.25 | 0.005 | 1000 | 411 | 1.10 | n.t. | 0.74 | 0.35 | 0.64 | n.t. |

TABLE 30-continued

| Form. no # | NaCl [mM] | Sucrose [% w/v] | Histidine [mM] | CaCl$_2$ [mM] | GSH [mM] | Tween ® 80 [% v/v] | dosage form [IU] | FVIII:C activity prior to freeze-drying [IU/ml] | Storage stability of lyophilisates: HMWC by SE-HPLC [%] (n.t. = not tested) |||||
|---|---|---|---|---|---|---|---|---|---|---|---|---|---|
| | | | | | | | | | after FD (Time 0) | +40° C. ||||
| | | | | | | | | | | 1 month | 3 month | 6 month | 9 month | 12 month |
| 09-004 | 65 | 5.0 | 55 | 10 | 0.25 | 0.005 | 1000 | 389 | 0.30 | n.t. | 1.00 | 0.76 | 1.10 | n.t. |
| 09-005 | 65 | 5.0 | 30 | 10 | 0.25 | 0.005 | 1000 | 383 | 0.26 | n.t. | 0.88 | 0.69 | 1.13 | n.t. |
| 09-006 | 65 | 5.0 | 10 | 10 | 0.25 | 0.005 | 1000 | 384 | 0.25 | n.t. | 0.98 | 1.03 | 1.26 | n.t. |

Example 10

FVIII:C Chromogenic Substrate Activity Assay and HMWC Formation (SE-HPLC) in Freeze-Dried Preparations Upon Storage at Elevated Temperature.

The FVIII:C activity and the concentration of the excipients were adjusted by diluting a FVIII concentrate (CSL627) with appropriate buffer solutions. The solutions were then dispensed (2.5 mL) and freeze-dried. The obtained lyophilisates were stored at +40° C. and samples taken after 3, 6 and 9 months. Samples were taken from the reconstituted solutions prior to and following storage of the lyophilisates and frozen at −70° C. HMWC were determined in the samples stored frozen following thawing in a water bath (+37° C.).

FVIII:C activity (Chromogenic substrate FVIII activity assay) was determined in the fresh solutions prior to freeze-drying and in the fresh reconstituted lyophilisates directly following freeze-drying or after storage. The recovery (stability) was calculated as the percentage of FVIII:C after storage divided by the FVIII:C activity at Time 0. The FVIII:C activity at Time 0 (After freeze-drying) was defined as 100%.

TABLE 31

| Form. no # | NaCl [mM] | Sucrose [% w/v] | Histidine [mM] | CaCl$_2$ [mM] | GSH [mM] | Tween ® 80 [% v/v] | dosage form [IU] | FVIII:C activity prior to freeze-drying [IU/ml] | Storage stability of lyophilisates: FVIII:C Coamatic Recovery [%] |||
|---|---|---|---|---|---|---|---|---|---|---|---|
| | | | | | | | | | after FD (Time 0) | +40° C. |||
| | | | | | | | | | | 3 month | 6 month | 9 month |
| 10-001 | 65 | 5.0 | 100 | 10 | 0.25 | 0.005 | 250 | 91 | 100 | 96 | 92 | 95 |
| 10-002 | 65 | 5.0 | 100 | 10 | 0.25 | 0.005 | 1000 | 402 | 100 | 99 | 88 | 96 |
| 10-003 | 65 | 5.0 | 100 | 10 | 0.25 | 0.005 | 3000 | 1340 | 100 | 90 | 85 | 87 |

TABLE 32

| Form. no # | NaCl [mM] | Sucrose [% w/v] | Histidine [mM] | CaCl$_2$ [mM] | L-Methionine [mM] | Tween ® 80 [% v/v] | dosage form [IU] | FVIII:C activity prior to freeze-drying [IU/ml] | Storage stability of lyophilisates: FVIII:C Coamatic Recovery [%] |||
|---|---|---|---|---|---|---|---|---|---|---|---|
| | | | | | | | | | after FD (Time 0) | +40° C. |||
| | | | | | | | | | | 3 month | 6 month | 9 month |
| 10-004 | 65 | 5.0 | 100 | 10 | 5.0 | 0.005 | 250 | 96 | 100 | 90 | 90 | 92 |
| 10-005 | 65 | 5.0 | 100 | 10 | 5.0 | 0.005 | 1000 | 416 | 100 | 96 | 97 | 90 |
| 10-006 | 65 | 5.0 | 100 | 10 | 5.0 | 0.005 | 3000 | 1324 | 100 | 97 | 93 | 94 |

TABLE 33

| Form. no # | NaCl [mM] | Sucrose [% w/v] | Histidine [mM] | CaCl$_2$ [mM] | GSH [mM] | Tween ® 80 [% v/v] | dosage form [IU] | FVIII:C activity prior to freeze-drying [IU/ml] | Storage stability of lyophilisates: HMWC by SE-HPLC [%] |||
|---|---|---|---|---|---|---|---|---|---|---|---|
| | | | | | | | | | after FD (Time 0) | +40° C. |||
| | | | | | | | | | | 3 month | 6 month | 9 month |
| 10-001 | 65 | 5.0 | 100 | 10 | 0.25 | 0.005 | 250 | 91 | 0.28 | 0.43 | 0.60 | 0.86 |
| 10-002 | 65 | 5.0 | 100 | 10 | 0.25 | 0.005 | 1000 | 402 | 0.36 | 0.39 | 1.01 | 1.05 |
| 10-003 | 65 | 5.0 | 100 | 10 | 0.25 | 0.005 | 3000 | 1340 | 0.55 | 0.55 | 1.00 | 1.08 |

TABLE 34

| | | | | | | | | Storage stability of lyophilisates: HMWC by SE-HPLC [%] | | | |
|---|---|---|---|---|---|---|---|---|---|---|---|
| | | | | | | | FVIII:C activity | | | | |
| | NaCl | Sucrose | Histidine | CaCl$_2$ | L-Methionine | Tween® 80 | dosage form | prior to freeze-drying | after FD (Time | +40° C. | | |
| Form. no # | [mM] | [% w/v] | [mM] | [mM] | [mM] | [% v/v] | [IU] | [IU/ml] | 0) | 3 month | 6 month | 9 month |
| 10-004 | 65 | 5.0 | 100 | 10 | 5.0 | 0.005 | 250 | 96 | 0.33 | 0.23 | 0.59 | 0.56 |
| 10-005 | 65 | 5.0 | 100 | 10 | 5.0 | 0.005 | 1000 | 416 | 0.41 | 0.45 | 1.09 | 0.97 |
| 10-006 | 65 | 5.0 | 100 | 10 | 5.0 | 0.005 | 3000 | 1324 | 0.62 | 0.84 | 1.12 | 1.25 |

The invention claimed is:

1. An aqueous composition, comprising:
   a. a coagulation Factor VIII (FVIII) molecule;
   b. 40 to 195 mM of a sodium salt;
   c. histidine;
   d. at least 1 mM of a calcium salt; and
   e. a surfactant,
   wherein [His]+20*[Ca$^{2+}$]≥180 mM, wherein [Ca$^{2+}$] is the concentration of calcium ions in the aqueous composition in millimole per liter, and [His] is the concentration of histidine in the aqueous composition in millimole per liter, with the proviso that [His]>0, and wherein the osmolarity of the aqueous composition is 600 mOsmol/L or less.

2. The aqueous composition according to claim 1, wherein the concentration of the sodium salt in the aqueous composition is 45 to 95 mM.

3. The aqueous composition according to claim 1, wherein [His] is 5 to 200 mM.

4. The aqueous composition according to claim 1, wherein [Ca$^{2+}$] is 5 to 100 mM.

5. The aqueous composition according to claim 1, wherein the pH of the aqueous composition is from 5 to 9.

6. The aqueous composition according to claim 1, wherein the aqueous composition, upon (i) lyophilization, (ii) storage of the lyophilized composition at a temperature of +25° C. and a relative humidity of 40% for a period of 12 months, and (iii) subsequent reconstitution of the lyophilized composition in distilled water, has a recovery of FVIII:C activity of at least 80%, relative to the same aqueous composition upon (i) lyophilization and without storage of the lyophilized composition, and (ii) subsequent immediate reconstitution in distilled water.

7. The aqueous composition according to claim 1, wherein the aqueous composition retains at least 80% of its Factor VIII activity for at least 48 hours, when stored in the liquid state at 4° C.

8. The aqueous composition according to claim 1, wherein the calcium salt is calcium chloride.

9. The aqueous composition according to claim 1, wherein the sodium salt is sodium chloride.

10. The aqueous composition according to claim 1, wherein the composition further comprises a carbohydrate.

11. The aqueous composition according to claim 10, wherein the carbohydrate is sucrose.

12. The aqueous composition according to claim 10, wherein the concentration of the carbohydrate is 1 to 20% (w/w).

13. The aqueous composition according to claim 1, wherein the concentration of the surfactant is 0.001 to 0.2% (v/v).

14. The aqueous composition according to claim 1, wherein the surfactant is a non-naturally occurring surfactant.

15. The aqueous composition according to claim 1, wherein the aqueous composition further comprises at least one amino acid other than histidine.

16. The aqueous composition according to claim 15, wherein the at least one amino acid other than histidine is selected from the group consisting of arginine, asparagine, aspartic acid, glutamic acid, glutamine, lysine, methionine, phenylalanine, leucine, isoleucine, and combinations thereof.

17. The aqueous composition according to claim 1, wherein the aqueous composition further comprises at least one antioxidant.

18. The aqueous composition according to claim 17, wherein the at least one antioxidant is selected from the group consisting of reduced glutathione, methionine, cysteine, sodium sulfite, vitamin A, vitamin E, ascorbic acid, sodium ascorbate, and combinations thereof.

19. The aqueous composition according to claim 17, wherein the concentration of the at least one antioxidant is 0.05-100 mM.

20. The aqueous composition according to claim 1, wherein the FVIII molecule is a recombinantly produced FVIII molecule selected from (i) a B-domain deleted or truncated FVIII molecule, (ii) a two-chain FVIII molecule, (iii) a single-chain FVIII molecule, (iv) a FVIII molecule comprising a protective group or half-life extending moiety, (v) a fusion protein comprising a FVIII amino acid sequence fused to a heterologous amino acid sequence, and (vi) combinations thereof.

21. A composition produced by lyophilizing the aqueous composition according to claim 1.

22. An aqueous composition produced by reconstituting the lyophilized composition according to claim 21 with an aqueous solution.

23. A method of stabilizing a FVIII molecule, comprising mixing the components of claim 1 to obtain an aqueous composition and lyophilizing the aqueous composition.

24. A method of treating a blood coagulation disorder, comprising administering a pharmaceutically effective amount of the aqueous composition according to claim 1 to a subject suffering from the blood coagulation disorder.

* * * * *

SEQUENCE LISTING

<160> NUMBER OF SEQ ID NOS: 2

<210> SEQ ID NO 1
<211> LENGTH: 2332
<212> TYPE: PRT
<213> ORGANISM: Homo sapiens

<400> SEQUENCE: 1

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

```
Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asp Asn Ser Pro Ser Phe
                355                 360                 365

Ile Gln Ile Arg Ser Val Ala Lys Lys His Pro Lys Thr Trp Val His
            370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685
```

```
Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
            725                 730                 735

Ile Glu Pro Arg Ser Phe Ser Gln Asn Ser Arg His Arg Ser Thr Arg
                740                 745                 750

Gln Lys Gln Phe Asn Ala Thr Thr Ile Pro Glu Asn Asp Ile Glu Lys
            755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
            885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
            915                 920                 925

Leu Thr Glu Ser Gly Gly Pro Leu Ser Leu Ser Glu Glu Asn Asn Asp
            930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
            965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
            995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
```

```
              1100                1105                1110

Gly Lys Asn Ser Leu Asn Ser Gly Gln Gly Pro Ser Pro Lys Gln
         1115                1120                1125

Leu Val Ser Leu Gly Pro Glu Lys Ser Val Glu Gly Gln Asn Phe
         1130                1135                1140

Leu Ser Glu Lys Asn Lys Val Val Gly Lys Gly Glu Phe Thr
         1145                1150                1155

Lys Asp Val Gly Leu Lys Glu Met Val Phe Pro Ser Ser Arg Asn
         1160                1165                1170

Leu Phe Leu Thr Asn Leu Asp Asn Leu His Glu Asn Asn Thr His
         1175                1180                1185

Asn Gln Glu Lys Lys Ile Gln Glu Ile Glu Lys Lys Glu Thr
         1190                1195                1200

Leu Ile Gln Glu Asn Val Val Leu Pro Gln Ile His Thr Val Thr
         1205                1210                1215

Gly Thr Lys Asn Phe Met Lys Asn Leu Phe Leu Leu Ser Thr Arg
         1220                1225                1230

Gln Asn Val Glu Gly Ser Tyr Asp Gly Ala Tyr Ala Pro Val Leu
         1235                1240                1245

Gln Asp Phe Arg Ser Leu Asn Asp Ser Thr Asn Arg Thr Lys Lys
         1250                1255                1260

His Thr Ala His Phe Ser Lys Lys Gly Glu Glu Glu Asn Leu Glu
         1265                1270                1275

Gly Leu Gly Asn Gln Thr Lys Gln Ile Val Glu Lys Tyr Ala Cys
         1280                1285                1290

Thr Thr Arg Ile Ser Pro Asn Thr Ser Gln Gln Asn Phe Val Thr
         1295                1300                1305

Gln Arg Ser Lys Arg Ala Leu Lys Gln Phe Arg Leu Pro Leu Glu
         1310                1315                1320

Glu Thr Glu Leu Glu Lys Arg Ile Ile Val Asp Asp Thr Ser Thr
         1325                1330                1335

Gln Trp Ser Lys Asn Met Lys His Leu Thr Pro Ser Thr Leu Thr
         1340                1345                1350

Gln Ile Asp Tyr Asn Glu Lys Glu Lys Gly Ala Ile Thr Gln Ser
         1355                1360                1365

Pro Leu Ser Asp Cys Leu Thr Arg Ser His Ser Ile Pro Gln Ala
         1370                1375                1380

Asn Arg Ser Pro Leu Pro Ile Ala Lys Val Ser Ser Phe Pro Ser
         1385                1390                1395

Ile Arg Pro Ile Tyr Leu Thr Arg Val Leu Phe Gln Asp Asn Ser
         1400                1405                1410

Ser His Leu Pro Ala Ala Ser Tyr Arg Lys Lys Asp Ser Gly Val
         1415                1420                1425

Gln Glu Ser Ser His Phe Leu Gln Gly Ala Lys Lys Asn Asn Leu
         1430                1435                1440

Ser Leu Ala Ile Leu Thr Leu Glu Met Thr Gly Asp Gln Arg Glu
         1445                1450                1455

Val Gly Ser Leu Gly Thr Ser Ala Thr Asn Ser Val Thr Tyr Lys
         1460                1465                1470

Lys Val Glu Asn Thr Val Leu Pro Lys Pro Asp Leu Pro Lys Thr
         1475                1480                1485

Ser Gly Lys Val Glu Leu Leu Pro Lys Val His Ile Tyr Gln Lys
         1490                1495                1500
```

```
Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
1595                1600                1605

Ala Ile Ala Ala Ile Asn Glu Gly Gln Asn Lys Pro Glu Ile Glu
1610                1615                1620

Val Thr Trp Ala Lys Gln Gly Arg Thr Glu Arg Leu Cys Ser Gln
1625                1630                1635

Asn Pro Pro Val Leu Lys Arg His Gln Arg Glu Ile Thr Arg Thr
1640                1645                1650

Thr Leu Gln Ser Asp Gln Glu Glu Ile Asp Tyr Asp Asp Thr Ile
1655                1660                1665

Ser Val Glu Met Lys Lys Glu Asp Phe Asp Ile Tyr Asp Glu Asp
1670                1675                1680

Glu Asn Gln Ser Pro Arg Ser Phe Gln Lys Lys Thr Arg His Tyr
1685                1690                1695

Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860

Asn Pro Ala His Gly Arg Gln Val Thr Val Gln Glu Phe Ala Leu
1865                1870                1875

Phe Phe Thr Ile Phe Asp Glu Thr Lys Ser Trp Tyr Phe Thr Glu
1880                1885                1890
```

```
Asn Met Glu Arg Asn Cys Arg Ala Pro Cys Asn Ile Gln Met Glu
1895               1900               1905

Asp Pro Thr Phe Lys Glu Asn Tyr Arg Phe His Ala Ile Asn Gly
1910               1915               1920

Tyr Ile Met Asp Thr Leu Pro Gly Leu Val Met Ala Gln Asp Gln
1925               1930               1935

Arg Ile Arg Trp Tyr Leu Leu Ser Met Gly Ser Asn Glu Asn Ile
1940               1945               1950

His Ser Ile His Phe Ser Gly His Val Phe Thr Val Arg Lys Lys
1955               1960               1965

Glu Glu Tyr Lys Met Ala Leu Tyr Asn Leu Tyr Pro Gly Val Phe
1970               1975               1980

Glu Thr Val Glu Met Leu Pro Ser Lys Ala Gly Ile Trp Arg Val
1985               1990               1995

Glu Cys Leu Ile Gly Glu His Leu His Ala Gly Met Ser Thr Leu
2000               2005               2010

Phe Leu Val Tyr Ser Asn Lys Cys Gln Thr Pro Leu Gly Met Ala
2015               2020               2025

Ser Gly His Ile Arg Asp Phe Gln Ile Thr Ala Ser Gly Gln Tyr
2030               2035               2040

Gly Gln Trp Ala Pro Lys Leu Ala Arg Leu His Tyr Ser Gly Ser
2045               2050               2055

Ile Asn Ala Trp Ser Thr Lys Glu Pro Phe Ser Trp Ile Lys Val
2060               2065               2070

Asp Leu Leu Ala Pro Met Ile Ile His Gly Ile Lys Thr Gln Gly
2075               2080               2085

Ala Arg Gln Lys Phe Ser Ser Leu Tyr Ile Ser Gln Phe Ile Ile
2090               2095               2100

Met Tyr Ser Leu Asp Gly Lys Lys Trp Gln Thr Tyr Arg Gly Asn
2105               2110               2115

Ser Thr Gly Thr Leu Met Val Phe Phe Gly Asn Val Asp Ser Ser
2120               2125               2130

Gly Ile Lys His Asn Ile Phe Asn Pro Pro Ile Ile Ala Arg Tyr
2135               2140               2145

Ile Arg Leu His Pro Thr His Tyr Ser Ile Arg Ser Thr Leu Arg
2150               2155               2160

Met Glu Leu Met Gly Cys Asp Leu Asn Ser Cys Ser Met Pro Leu
2165               2170               2175

Gly Met Glu Ser Lys Ala Ile Ser Asp Ala Gln Ile Thr Ala Ser
2180               2185               2190

Ser Tyr Phe Thr Asn Met Phe Ala Thr Trp Ser Pro Ser Lys Ala
2195               2200               2205

Arg Leu His Leu Gln Gly Arg Ser Asn Ala Trp Arg Pro Gln Val
2210               2215               2220

Asn Asn Pro Lys Glu Trp Leu Gln Val Asp Phe Gln Lys Thr Met
2225               2230               2235

Lys Val Thr Gly Val Thr Thr Gln Gly Val Lys Ser Leu Leu Thr
2240               2245               2250

Ser Met Tyr Val Lys Glu Phe Leu Ile Ser Ser Ser Gln Asp Gly
2255               2260               2265

His Gln Trp Thr Leu Phe Phe Gln Asn Gly Lys Val Lys Val Phe
2270               2275               2280

Gln Gly Asn Gln Asp Ser Phe Thr Pro Val Val Asn Ser Leu Asp
```

```
                     2285                2290                2295
Pro  Pro  Leu  Leu  Thr  Arg  Tyr  Leu  Arg  Ile  His  Pro  Gln  Ser  Trp
              2300                2305                2310

Val  His  Gln  Ile  Ala  Leu  Arg  Met  Glu  Val  Leu  Gly  Cys  Glu  Ala
              2315                2320                2325

Gln  Asp  Leu  Tyr
              2330

<210> SEQ ID NO 2
<211> LENGTH: 1444
<212> TYPE: PRT
<213> ORGANISM: Artificial Sequence
<220> FEATURE:
<223> OTHER INFORMATION: single chain FVIII dBN(64-53)

<400> SEQUENCE: 2

Ala  Thr  Arg  Arg  Tyr  Tyr  Leu  Gly  Ala  Val  Glu  Leu  Ser  Trp  Asp  Tyr
 1                   5                   10                  15

Met  Gln  Ser  Asp  Leu  Gly  Glu  Leu  Pro  Val  Asp  Ala  Arg  Phe  Pro  Pro
                20                  25                  30

Arg  Val  Pro  Lys  Ser  Phe  Pro  Phe  Asn  Thr  Ser  Val  Val  Tyr  Lys  Lys
             35                  40                  45

Thr  Leu  Phe  Val  Glu  Phe  Thr  Asp  His  Leu  Phe  Asn  Ile  Ala  Lys  Pro
         50                  55                  60

Arg  Pro  Pro  Trp  Met  Gly  Leu  Leu  Gly  Pro  Thr  Ile  Gln  Ala  Glu  Val
65                   70                  75                  80

Tyr  Asp  Thr  Val  Val  Ile  Thr  Leu  Lys  Asn  Met  Ala  Ser  His  Pro  Val
                 85                  90                  95

Ser  Leu  His  Ala  Val  Gly  Val  Ser  Tyr  Trp  Lys  Ala  Ser  Glu  Gly  Ala
             100                 105                 110

Glu  Tyr  Asp  Asp  Gln  Thr  Ser  Gln  Arg  Glu  Lys  Glu  Asp  Asp  Lys  Val
         115                 120                 125

Phe  Pro  Gly  Gly  Ser  His  Thr  Tyr  Val  Trp  Gln  Val  Leu  Lys  Glu  Asn
     130                 135                 140

Gly  Pro  Met  Ala  Ser  Asp  Pro  Leu  Cys  Leu  Thr  Tyr  Ser  Tyr  Leu  Ser
145                 150                 155                 160

His  Val  Asp  Leu  Val  Lys  Asp  Leu  Asn  Ser  Gly  Leu  Ile  Gly  Ala  Leu
                 165                 170                 175

Leu  Val  Cys  Arg  Glu  Gly  Ser  Leu  Ala  Lys  Glu  Lys  Thr  Gln  Thr  Leu
             180                 185                 190

His  Lys  Phe  Ile  Leu  Leu  Phe  Ala  Val  Phe  Asp  Glu  Gly  Lys  Ser  Trp
         195                 200                 205

His  Ser  Glu  Thr  Lys  Asn  Ser  Leu  Met  Gln  Asp  Arg  Asp  Ala  Ala  Ser
     210                 215                 220

Ala  Arg  Ala  Trp  Pro  Lys  Met  His  Thr  Val  Asn  Gly  Tyr  Val  Asn  Arg
225                 230                 235                 240

Ser  Leu  Pro  Gly  Leu  Ile  Gly  Cys  His  Arg  Lys  Ser  Val  Tyr  Trp  His
                 245                 250                 255

Val  Ile  Gly  Met  Gly  Thr  Thr  Pro  Glu  Val  His  Ser  Ile  Phe  Leu  Glu
             260                 265                 270

Gly  His  Thr  Phe  Leu  Val  Arg  Asn  His  Arg  Gln  Ala  Ser  Leu  Glu  Ile
         275                 280                 285

Ser  Pro  Ile  Thr  Phe  Leu  Thr  Ala  Gln  Thr  Leu  Leu  Met  Asp  Leu  Gly
     290                 295                 300

Gln  Phe  Leu  Leu  Phe  Cys  His  Ile  Ser  Ser  His  Gln  His  Asp  Gly  Met
```

-continued

```
            305                 310                 315                 320
        Glu Ala Tyr Val Lys Val Asp Ser Cys Pro Glu Glu Pro Gln Leu Arg
                        325                 330                 335
        Met Lys Asn Asn Glu Glu Ala Glu Asp Tyr Asp Asp Leu Thr Asp
                        340                 345                 350
        Ser Glu Met Asp Val Val Arg Phe Asp Asp Asn Ser Pro Ser Phe
                        355                 360                 365
        Ile Gln Ile Arg Ser Val Ala Lys Lys His Pro Lys Thr Trp Val His
                370                 375                 380
        Tyr Ile Ala Ala Glu Glu Asp Trp Asp Tyr Ala Pro Leu Val Leu
        385                 390                 395                 400
        Ala Pro Asp Asp Arg Ser Tyr Lys Ser Gln Tyr Leu Asn Asn Gly Pro
                        405                 410                 415
        Gln Arg Ile Gly Arg Lys Tyr Lys Val Arg Phe Met Ala Tyr Thr
                        420                 425                 430
        Asp Glu Thr Phe Lys Thr Arg Glu Ala Ile Gln His Glu Ser Gly Ile
                        435                 440                 445
        Leu Gly Pro Leu Leu Tyr Gly Glu Val Gly Asp Thr Leu Leu Ile Ile
                450                 455                 460
        Phe Lys Asn Gln Ala Ser Arg Pro Tyr Asn Ile Tyr Pro His Gly Ile
        465                 470                 475                 480
        Thr Asp Val Arg Pro Leu Tyr Ser Arg Arg Leu Pro Lys Gly Val Lys
                        485                 490                 495
        His Leu Lys Asp Phe Pro Ile Leu Pro Gly Glu Ile Phe Lys Tyr Lys
                        500                 505                 510
        Trp Thr Val Thr Val Glu Asp Gly Pro Thr Lys Ser Asp Pro Arg Cys
                        515                 520                 525
        Leu Thr Arg Tyr Tyr Ser Ser Phe Val Asn Met Glu Arg Asp Leu Ala
                        530                 535                 540
        Ser Gly Leu Ile Gly Pro Leu Leu Ile Cys Tyr Lys Glu Ser Val Asp
        545                 550                 555                 560
        Gln Arg Gly Asn Gln Ile Met Ser Asp Lys Arg Asn Val Ile Leu Phe
                        565                 570                 575
        Ser Val Phe Asp Glu Asn Arg Ser Trp Tyr Leu Thr Glu Asn Ile Gln
                        580                 585                 590
        Arg Phe Leu Pro Asn Pro Ala Gly Val Gln Leu Glu Asp Pro Glu Phe
                        595                 600                 605
        Gln Ala Ser Asn Ile Met His Ser Ile Asn Gly Tyr Val Phe Asp Ser
                        610                 615                 620
        Leu Gln Leu Ser Val Cys Leu His Glu Val Ala Tyr Trp Tyr Ile Leu
        625                 630                 635                 640
        Ser Ile Gly Ala Gln Thr Asp Phe Leu Ser Val Phe Phe Ser Gly Tyr
                        645                 650                 655
        Thr Phe Lys His Lys Met Val Tyr Glu Asp Thr Leu Thr Leu Phe Pro
                        660                 665                 670
        Phe Ser Gly Glu Thr Val Phe Met Ser Met Glu Asn Pro Gly Leu Trp
                        675                 680                 685
        Ile Leu Gly Cys His Asn Ser Asp Phe Arg Asn Arg Gly Met Thr Ala
                        690                 695                 700
        Leu Leu Lys Val Ser Ser Cys Asp Lys Asn Thr Gly Asp Tyr Tyr Glu
        705                 710                 715                 720
        Asp Ser Tyr Glu Asp Ile Ser Ala Tyr Leu Leu Ser Lys Asn Asn Ala
                        725                 730                 735
```

```
Ile Glu Pro Arg Ser Phe Ser Gln Asn Ser Arg His Pro Ser Thr Arg
        740                 745                 750

Gln Lys Gln Phe Asn Ala Thr Thr Ile Pro Glu Asn Thr Thr Leu Gln
        755                 760                 765

Ser Asp Gln Glu Glu Ile Asp Tyr Asp Thr Ile Ser Val Glu Met
770                 775                 780

Lys Lys Glu Asp Phe Asp Ile Tyr Asp Glu Asp Glu Asn Gln Ser Pro
785                 790                 795                 800

Arg Ser Phe Gln Lys Lys Thr Arg His Tyr Phe Ile Ala Ala Val Glu
            805                 810                 815

Arg Leu Trp Asp Tyr Gly Met Ser Ser Pro His Val Leu Arg Asn
        820                 825                 830

Arg Ala Gln Ser Gly Ser Val Pro Gln Phe Lys Lys Val Val Phe Gln
        835                 840                 845

Glu Phe Thr Asp Gly Ser Phe Thr Gln Pro Leu Tyr Arg Gly Glu Leu
        850                 855                 860

Asn Glu His Leu Gly Leu Leu Gly Pro Tyr Ile Arg Ala Glu Val Glu
865                 870                 875                 880

Asp Asn Ile Met Val Thr Phe Arg Asn Gln Ala Ser Arg Pro Tyr Ser
                885                 890                 895

Phe Tyr Ser Ser Leu Ile Ser Tyr Glu Glu Asp Gln Arg Gln Gly Ala
                900                 905                 910

Glu Pro Arg Lys Asn Phe Val Lys Pro Asn Glu Thr Lys Thr Tyr Phe
        915                 920                 925

Trp Lys Val Gln His His Met Ala Pro Thr Lys Asp Glu Phe Asp Cys
        930                 935                 940

Lys Ala Trp Ala Tyr Phe Ser Asp Val Asp Leu Glu Lys Asp Val His
945                 950                 955                 960

Ser Gly Leu Ile Gly Pro Leu Leu Val Cys His Thr Asn Thr Leu Asn
                965                 970                 975

Pro Ala His Gly Arg Gln Val Thr Val Gln Glu Phe Ala Leu Phe Phe
                980                 985                 990

Thr Ile Phe Asp Glu Thr Lys Ser Trp Tyr Phe Thr Glu Asn Met Glu
        995                 1000                1005

Arg Asn Cys Arg Ala Pro Cys Asn Ile Gln Met Glu Asp Pro Thr
    1010                1015                1020

Phe Lys Glu Asn Tyr Arg Phe His Ala Ile Asn Gly Tyr Ile Met
    1025                1030                1035

Asp Thr Leu Pro Gly Leu Val Met Ala Gln Asp Gln Arg Ile Arg
    1040                1045                1050

Trp Tyr Leu Leu Ser Met Gly Ser Asn Glu Asn Ile His Ser Ile
    1055                1060                1065

His Phe Ser Gly His Val Phe Thr Val Arg Lys Lys Glu Glu Tyr
    1070                1075                1080

Lys Met Ala Leu Tyr Asn Leu Tyr Pro Gly Val Phe Glu Thr Val
    1085                1090                1095

Glu Met Leu Pro Ser Lys Ala Gly Ile Trp Arg Val Glu Cys Leu
    1100                1105                1110

Ile Gly Glu His Leu His Ala Gly Met Ser Thr Leu Phe Leu Val
    1115                1120                1125

Tyr Ser Asn Lys Cys Gln Thr Pro Leu Gly Met Ala Ser Gly His
    1130                1135                1140
```

```
Ile Arg Asp Phe Gln Ile Thr Ala Ser Gly Gln Tyr Gly Gln Trp
    1145                1150                1155

Ala Pro Lys Leu Ala Arg Leu His Tyr Ser Gly Ser Ile Asn Ala
    1160                1165                1170

Trp Ser Thr Lys Glu Pro Phe Ser Trp Ile Lys Val Asp Leu Leu
    1175                1180                1185

Ala Pro Met Ile Ile His Gly Ile Lys Thr Gln Gly Ala Arg Gln
    1190                1195                1200

Lys Phe Ser Ser Leu Tyr Ile Ser Gln Phe Ile Ile Met Tyr Ser
    1205                1210                1215

Leu Asp Gly Lys Lys Trp Gln Thr Tyr Arg Gly Asn Ser Thr Gly
    1220                1225                1230

Thr Leu Met Val Phe Phe Gly Asn Val Asp Ser Ser Gly Ile Lys
    1235                1240                1245

His Asn Ile Phe Asn Pro Pro Ile Ile Ala Arg Tyr Ile Arg Leu
    1250                1255                1260

His Pro Thr His Tyr Ser Ile Arg Ser Thr Leu Arg Met Glu Leu
    1265                1270                1275

Met Gly Cys Asp Leu Asn Ser Cys Ser Met Pro Leu Gly Met Glu
    1280                1285                1290

Ser Lys Ala Ile Ser Asp Ala Gln Ile Thr Ala Ser Ser Tyr Phe
    1295                1300                1305

Thr Asn Met Phe Ala Thr Trp Ser Pro Ser Lys Ala Arg Leu His
    1310                1315                1320

Leu Gln Gly Arg Ser Asn Ala Trp Arg Pro Gln Val Asn Asn Pro
    1325                1330                1335

Lys Glu Trp Leu Gln Val Asp Phe Gln Lys Thr Met Lys Val Thr
    1340                1345                1350

Gly Val Thr Thr Gln Gly Val Lys Ser Leu Leu Thr Ser Met Tyr
    1355                1360                1365

Val Lys Glu Phe Leu Ile Ser Ser Ser Gln Asp Gly His Gln Trp
    1370                1375                1380

Thr Leu Phe Phe Gln Asn Gly Lys Val Lys Val Phe Gln Gly Asn
    1385                1390                1395

Gln Asp Ser Phe Thr Pro Val Val Asn Ser Leu Asp Pro Pro Leu
    1400                1405                1410

Leu Thr Arg Tyr Leu Arg Ile His Pro Gln Ser Trp Val His Gln
    1415                1420                1425

Ile Ala Leu Arg Met Glu Val Leu Gly Cys Glu Ala Gln Asp Leu
    1430                1435                1440

Tyr
```